US012670975B2

(12) United States Patent
Amarasingham et al.

(10) Patent No.: US 12,670,975 B2
(45) Date of Patent: ***Jun. 30, 2026

(54) CREATING MULTIPLE PRIORITIZED CLINICAL SUMMARIES USING ARTIFICIAL INTELLIGENCE

(71) Applicant: Pieces Technologies, Inc., Irving, TX (US)

(72) Inventors: Rubendran Amarasingham, Farmers Branch, TX (US); Yukun Chen, Carrolton, TX (US); Komli-Kofi Atsina, Jr., Coppell, TX (US); Sherene Philip, Dallas, TX (US); Hong Kang, Frisco, TX (US)

(73) Assignee: Pieces Technologies, Inc., Irving, TX (US)

( * ) Notice: Subject to any disclaimer, the term of this patent is extended or adjusted under 35 U.S.C. 154(b) by 95 days.

This patent is subject to a terminal disclaimer.

(21) Appl. No.: 18/673,498

(22) Filed: May 24, 2024

(65) Prior Publication Data

US 2024/0312583 A1 Sep. 19, 2024

Related U.S. Application Data

(63) Continuation of application No. 17/959,484, filed on Oct. 4, 2022, now Pat. No. 12,014,808.

(Continued)

(51) Int. Cl.
*G16H 15/00* (2018.01)

(52) U.S. Cl.
CPC .................................... *G16H 15/00* (2018.01)

(58) Field of Classification Search
CPC ........ G16H 10/60; G16H 15/00; G16H 20/00; G16H 50/30; G06F 40/30; G06F 40/295; G06F 40/205

(Continued)

(56) References Cited

U.S. PATENT DOCUMENTS 9,536,052 B2 1/2017 Amarasingham et al.
10,740,064 B1 * 8/2020 Reddy ................... G11B 27/031
(Continued)

FOREIGN PATENT DOCUMENTS

CN 110188358 A 8/2019

OTHER PUBLICATIONS

International Search Report and Written Opinion mailed Dec. 15, 2022 in International Application No. PCT/US2022/077542, 23 pages.

(Continued)

*Primary Examiner* — Alaaeldin M. Elshaer
(74) *Attorney, Agent, or Firm* — Jordan IP Law, LLC

(57) ABSTRACT

A system, method, and a computer program product for generating a clinical summary of a patient using artificial intelligence is provided. A patient data that includes unstructured data and structured data is collected from multiple computing devices. Natural language processing models determine clinical issues from the unstructured data. Active clinical issues are determined from the clinical issues. A knowledge graph generated using a relational language model determines treatments associated with the active clinical issues. Active diagnostic and treatment orders are determined from the structured data. Multiple summaries summarizing the active clinical issues, treatments, active diagnostic orders, and active treatment orders are determined using natural language generation models trained to summarize multiple tasks. The multiple summaries are aggregated into a single summary. The language of the summary is modified using a hyperparameter in a smoothing natural language model to direct the summary toward an audience having a particular type.

20 Claims, 12 Drawing Sheets

Related U.S. Application Data

(60) Provisional application No. 63/252,518, filed on Oct. 5, 2021.

(58) Field of Classification Search
USPC ......................................................... 703/2, 3
See application file for complete search history.

(56) References Cited

U.S. PATENT DOCUMENTS

| | | | |
|---|---|---|---|
| 11,045,271 B1 | 6/2021 | Tran | |
| 2014/0172456 A1* | 6/2014 | Qian | G06F 40/237 |
| | | | 705/3 |
| 2015/0193583 A1 | 7/2015 | McNair et al. | |
| 2016/0019299 A1 | 1/2016 | Boloor et al. | |
| 2016/0162456 A1* | 6/2016 | Munro | G06F 16/24532 |
| | | | 704/9 |
| 2017/0046311 A1 | 2/2017 | Walker | |
| 2017/0076046 A1* | 3/2017 | Barnes | G16H 10/60 |
| 2017/0132371 A1 | 5/2017 | Amarasingham et al. | |
| 2019/0034590 A1* | 1/2019 | Oren | G16H 10/60 |
| 2019/0189253 A1 | 6/2019 | Kartoun et al. | |
| 2020/0057946 A1 | 2/2020 | Singaraju et al. | |
| 2020/0320249 A1 | 10/2020 | Hwang | |
| 2021/0098133 A1 | 4/2021 | Chowdhry et al. | |
| 2021/0142789 A1 | 5/2021 | Gurbani et al. | |
| 2021/0183498 A1 | 6/2021 | Kalafut et al. | |
| 2021/0241381 A1 | 8/2021 | Neumann | |
| 2021/0334462 A1* | 10/2021 | Kukreja | G06F 40/295 |
| 2022/0059228 A1 | 2/2022 | Chen et al. | |
| 2022/0293092 A1* | 9/2022 | Ding | G10L 15/16 |
| 2022/0391270 A1* | 12/2022 | Gnanasambandam | |
| | | | G16H 20/70 |
| 2022/0391591 A1 | 12/2022 | Ronen et al. | |
| 2024/0087700 A1* | 3/2024 | Gnanasambandam | |
| | | | G16H 10/60 |

OTHER PUBLICATIONS

International Preliminary Report on Patentability issued Apr. 9, 2024 in International Application No. PCT/US2022/077542, 11 pages.

Krittanawong et al., "Artificial Intelligence in Global Health," European Heart Journal, vol. 42, Issue 24, Jun. 21, 2021, pp. 2321-2322.

Lim et al., "Subsentence Extraction from Text Using Coverage-Based Deep Learning Language Models," Sensors 2021, vol. 21, 2021. [Retrieved from the Internet.] [Retrieved on May 23, 2024 from https://doi.org/10.3390/s21082712].

* cited by examiner

400

Request a summary of a patient condition from a user device associated with a type of a user ⟋ 402

Receive a summary of a patient's condition that corresponds to the type of the user ⟋ 404

Display the summary of the patient's condition on the user device in accordance with the type of the user ⟋ 406

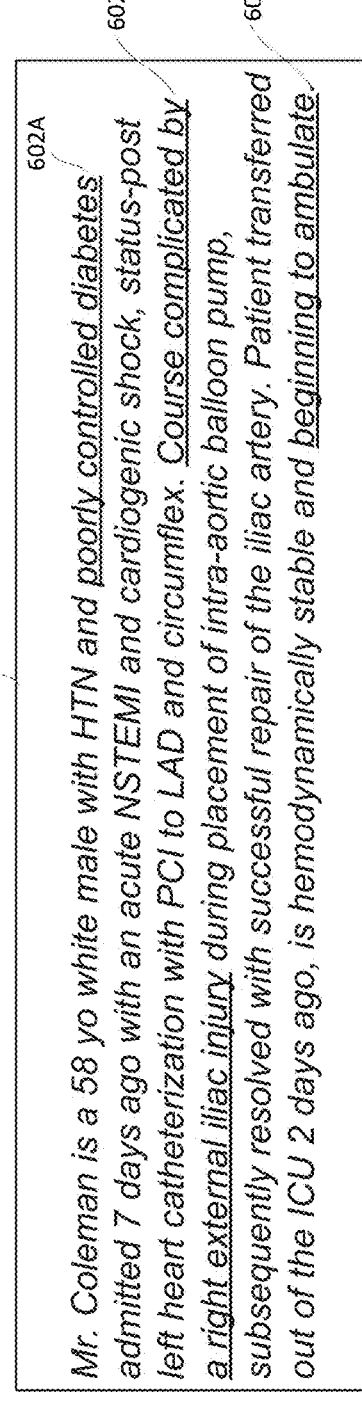

600A

114

602A

602B

602C

Mr. Coleman is a 58 yo white male with HTN and poorly controlled diabetes admitted 7 days ago with an acute NSTEMI and cardiogenic shock, status-post left heart catheterization with PCI to LAD and circumflex. Course complicated by a right external iliac injury during placement of intra-aortic balloon pump, subsequently resolved with successful repair of the iliac artery. Patient transferred out of the ICU 2 days ago, is hemodynamically stable and beginning to ambulate.

*Mr. Coleman is a 58 yo white male with HTN and poorly controlled diabetes (hbA1c 2 weeks ago was >9.5%) admitted 7 days ago with an acute NSTEMI and cardiogenic shock, status-post left heart catheterization with PCI to LAD and circumflex. Course complicated by a right external iliac injury during placement of intra-aortic balloon pump, subsequently resolved with successful repair of the iliac artery. Patient transferred out of the ICU 2 days ago, is hemodynamically stable and beginning to ambulate.*

*Mr. Coleman is a 58 yo white male with HTN and poorly controlled diabetes (hbA1c 2 weeks ago was >9.5%) admitted 7 days ago with an acute NSTEMI and cardiogenic shock, status-post left heart catheterization with PCI to LAD and circumflex. Course complicated by a right external iliac injury during placement of intra-aortic balloon pump, subsequently resolved with successful repair of the iliac artery. Patient transferred out of the ICU 2 days ago, is hemodynamically stable and beginning to ambulate. The patient is expected to improve.*

Figure 6D:
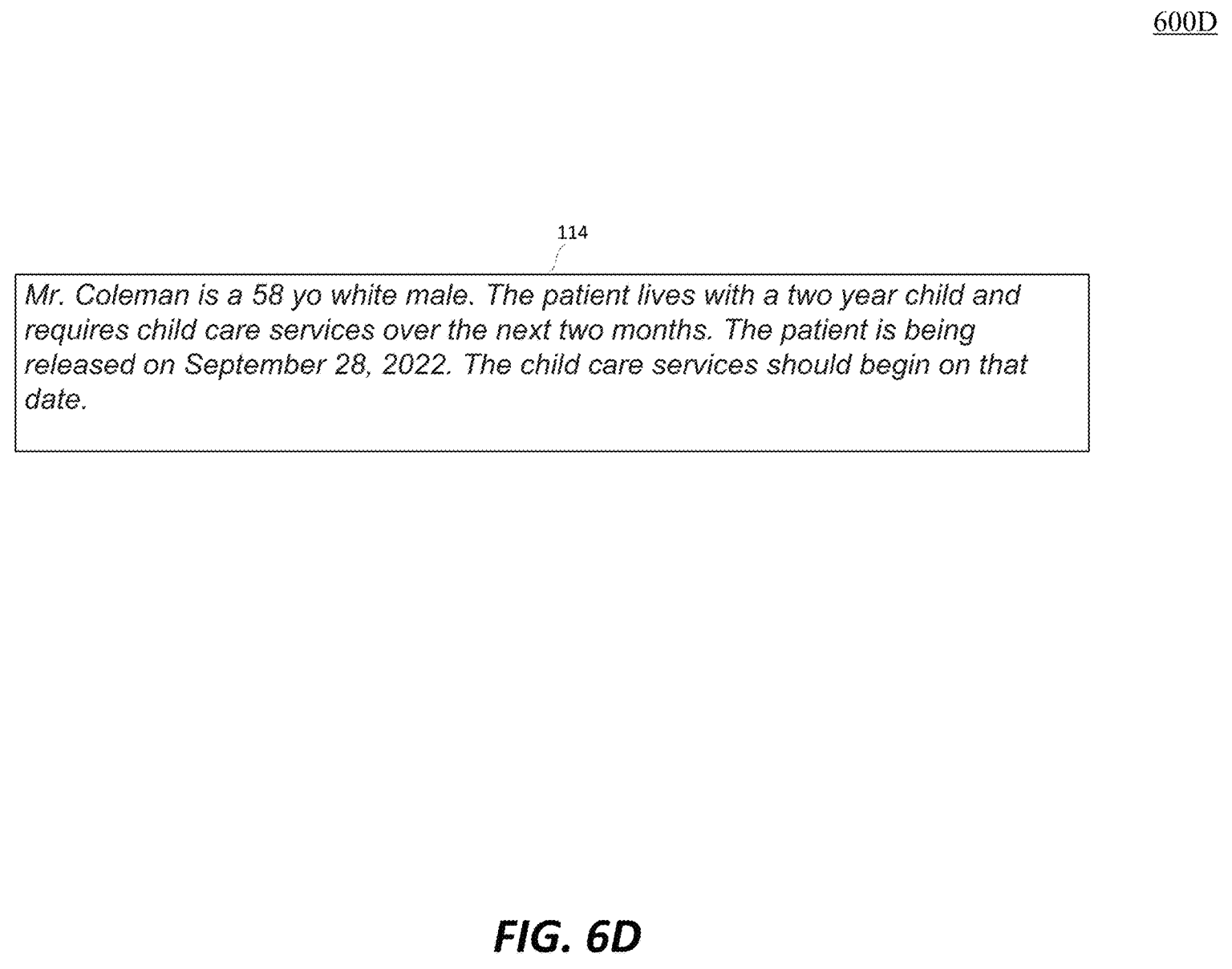

*Mr. Coleman is a 58 yo white male. The patient lives with a two year child and requires child care services over the next two months. The patient is being released on September 28, 2022. The child care services should begin on that date.*

CREATING MULTIPLE PRIORITIZED CLINICAL SUMMARIES USING ARTIFICIAL INTELLIGENCE

CROSS-REFERENCE TO RELATED APPLICATIONS

This application is a continuation of U.S. patent application Ser. No. 17/959,484, filed Oct. 4, 2022, now allowed, which claims priority under 35 U.S.C. § 119 to U.S. Provisional Application No. 63/252,518, filed Oct. 5, 2021, which are incorporated by reference herein in their entirety.

TECHNICAL FIELD

This application relates generally to natural language processing, natural language generation, and machine learning, and more specifically to using natural language processing and machine learning to generate a summary of a patient's medical status, risks and plan from structured and unstructured clinical and non-clinical data.

BACKGROUND

Conventionally, when physicians and doctors leave a hospital, the only record of a patient's health is a manual or online note written by one or more physicians or clinical teams attending to the patient. The comments provided by one doctor can be critical to the ongoing care of a patient provided by the next doctor. Since the number of patients for any one doctor can be quite high, the process of creating, updating and sharing notes and other documentation may leave a doctor with a large amount of time-consuming work with a naturally high error rate or infidelity of communication.

To save time, one approach is to create or update notes that focus on patient issues that are imminent to the patient's well-being and to leave other issues for a later time. Prioritization by a doctor is subject to human error and can overlook critical time-sensitive matters, leaving those unattended while other issues are included in a patient profile. For example, a patient may have a critical condition or chronic health condition that requires immediate attention. However, focusing on one seemingly critical issue may cause other conditions or imminent matters that are critical to the patient's health to be overlooked. If all conditions were identified and entered into a database, then there would be a higher chance that those conditions which affect both imminent and long-term health could be examined and addressed in a reasonable time frame. The reality is that the patient may receive a fraction of the beneficial treatment options before going home and may not return in time to have the other conditions reviewed, which could lead to adverse health outcomes.

Further, the quality of information that different physicians and doctors transfer into the patient documentation varies among different authors. As a result, the patient information may be entered into the system inaccurately, may not be entered at all, or may be difficult to find. Missing or inaccurate patient information may lead to errors in patient care.

A thoughtfully written summary provided at the time of a shift change, change in level of care or setting of care, or other care transition can reduce the likelihood of communication errors, improve the expediency of care, and reduce stress. However, generating such a summary is time consuming for the transferring physician or team and the summary may not be possible to generate or update once the transferring team has already left. Therefore, critical information may be latent or missing by the time the receiving team reviews the patient's record. What is needed is an automated way to generate a summary for the patient.

BRIEF DESCRIPTION OF THE DRAWINGS

FIGS. 6A-B are diagrams of summaries that include hyperlinks, according to some embodiments.

FIG. 6C is a diagram of an updated summary, according to some embodiments.

FIG. 6D is a diagram of a summary that includes social determinants, according to some embodiments.

Figure 1A:
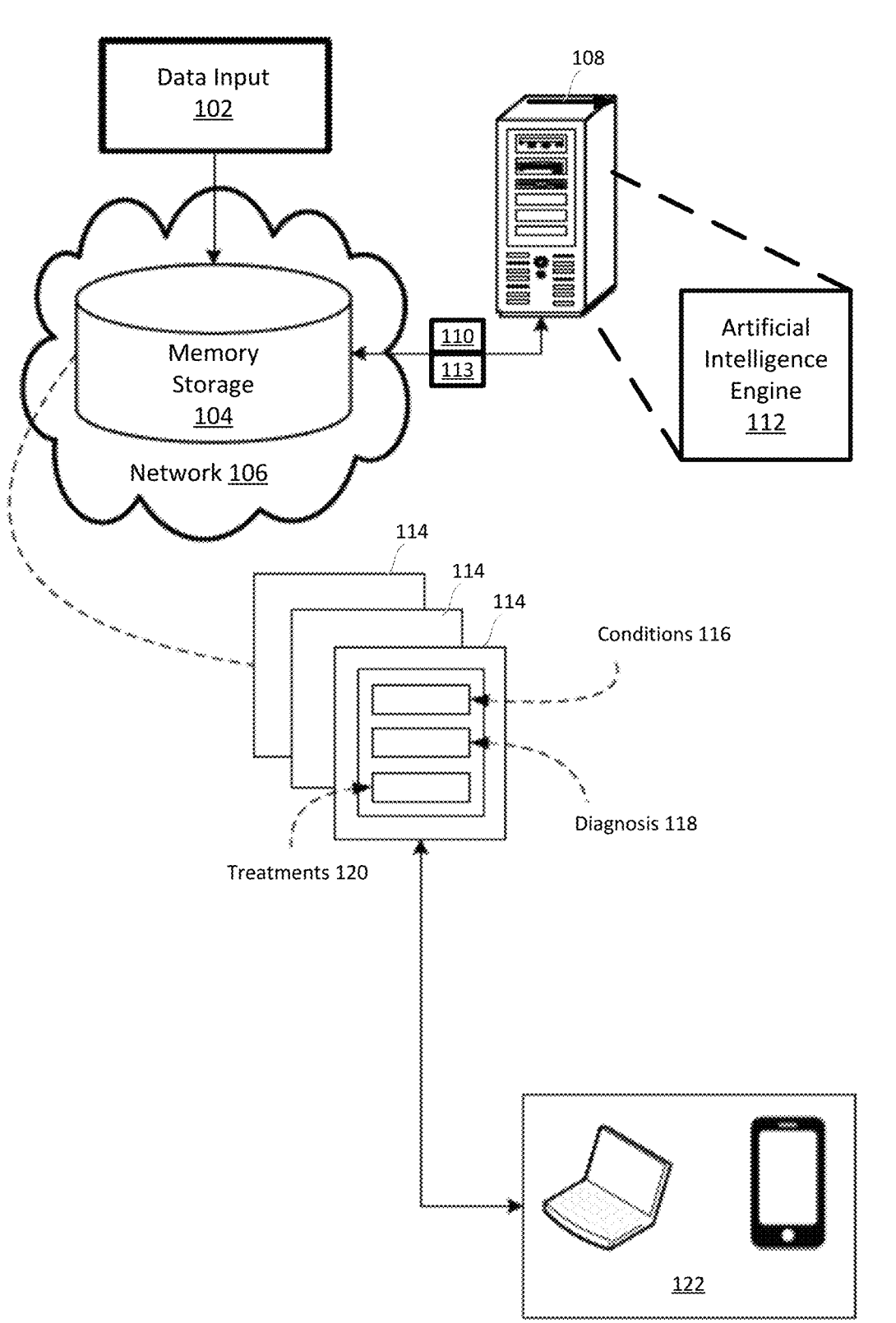
FIGS. 1A-1C are block diagrams illustrating an example patient profile management system for generating patient data and patient summaries according to some embodiments.

In one or more implementations, not all of the depicted components in each figure may be required, and one or more implementations may include additional components not shown in a figure. Variations in the arrangement and type of the components may be made without departing from the scope of the subject disclosure. Additional components, different components, or fewer components may be utilized within the scope of the subject disclosure.

DETAILED DESCRIPTION

It will be readily understood that the components of disclosure, as generally described and illustrated in the figures herein, may be arranged and designed in a wide variety of different configurations. Thus, the following detailed description of the embodiments of a method, apparatus, and system, as represented in the attached figures, is not intended to limit the scope of the application as claimed, but is merely representative of selected embodiments of the application.

The features, structures, or characteristics of the application described throughout this specification may be combined in any suitable manner in one or more embodiments. For example, the usage of the phrases "example embodiments", "some embodiments", or other similar language throughout this specification refers to the fact that a particular feature, structure, or characteristic described in connection with the embodiment may be included in at least one embodiment of the application. Thus, appearances of the phrases "example embodiments", "in some embodiments", "in other embodiments", or other similar language, throughout this specification do not necessarily all refer to the same group of embodiments, and the described features, structures, or characteristics may be combined in any suitable manner in one or more embodiments.

As used herein, the term "module" or "engine" may comprise any hardware or software-based framework that includes any artificial intelligence network or system, neural network or system and/or any training or learning models implemented thereon or therewith.

Example embodiments provide a module or a combination of modules that operate as software, firmware and/or hardware on a computing device to process information in a database or another memory storage to identify potentially relevant information, to summarize the information and to present the information in a modified format generated using artificial intelligence. For example, hospital, ambulatory, or patient-based medical records of patients and patient profile information may be identified and automatically processed to identify content of various inputs, such as a person, age, sex, reason for visiting the medical facility, current conditions, previous conditions, medications administered, etc. Also, the current conditions a patient may be experiencing can be identified and processed based on a knowledge base of information to achieve additional recommendations, diagnoses, procedures, tests, medications, treatments, etc., to assist the patients in their current health status. Additionally, the output may include a streamlined note or summary, and it may include different summaries tailored to various parties, such as doctors, nurses, patient, patient's family, etc. For example, the raw data summary generated from doctors' notes, medical tests, nurse charts, etc., may include all the current conditions, all the current diagnoses, and all the current recommendations for treatment, etc. A summary generated for a medical professional, e.g., a doctor may include specific terms by their technical names, which require imminent action, imminent treatment, imminent response and awareness for a patient's well-being. A summary generated for a patient or a family may include the patient's status in layman's terms, without using verbiage that may be confusing to a reader of the summary who is not familiar with the specific medical terms, procedures, treatments, etc. Additionally, the summary may be translated into a variety of languages, such as English to Spanish, French, Chinese, etc.

A patient management system may include artificial intelligence algorithms, natural language processors (NLPs), machine learning, word choice algorithms, etc., may receive patient data in structured and unstructured formats, process the data and generate patient summaries. The summaries serve as an instrument to patient care because the summaries allow physicians and nurses to access and navigate the patients' active clinical issues, orders, and treatments. This is an improvement over conventional techniques whether the patients' information is stored in multiple disparate systems, may not be entered at all into the system or entered belatedly due to physicians prioritizing other tasks.

A thoughtful auto-generated summary with pertinent information updated at the moment when the clinician is ready to consult it can best guide the care of the patient. The auto-generated summary is particularly beneficial during a medical team-to-medical team handover or other transitions between healthcare personnel or settings. An auto-generated summary can also solve a problem of proper and high fidelity communications taking place during each transition of care of the patient both within and outside the healthcare system. For example, when a patient leaves the hospital, the discharging physician team often communicates with the outpatient receiving physician team. Nurses often communicate or "sign out" critical information at each shift change. Ambulatory primary care physicians often communicate with the ambulatory specialist physicians. Health system personnel often communicates continuously with the patients and family members throughout and between health encounters. An auto-generated summary, particularly a summary directed to various audiences and at a readability level the audience can understand (e.g., a plain language summary for the patient) that convey key pertinent information, and that is updated continuously with the appropriate context, setting, readability and language of the user, would provide information that aligns patients, care teams, and family members, and also reduces the possibility of an error.

Further embodiments of the patient management system are discussed below.

FIG. 1A illustrates an example patient management system 100A where embodiments may be implemented. The patient management system 100A includes computing and storage components that receive, process, and summarize patient data, according to example embodiments. Patient management system 100A receives data input 102. Data input 102 may include medical input associated with a patient, including patient conditions, prescribed treatments, and/or diagnoses. Data input 102 may include numeric, textual, audio, and/or image data. One example of data input 102 may include hospital admission information that is collected by one or more computing devices when the patient arrives and is admitted to the hospital. Another example of data input 102 may be one or more patient vital signals received from various invasive and non-invasive medical devices and monitors, and may include devices such as heart monitor, respiratory monitor, thermometer, blood pressure monitor, etc. Another example of data input 102 may be medical notes written with an input device, such as a pen, stylus, keyboard, mouse, etc., that are scanned or received by a computing device of a medical professional. Another example of data input 102 may be audio data that a doctor records and that a computing device at a hospital receives as an audio file. Another example of data input 102 may include image results, such as magnetic resonance imaging (MRI), computed tomography (CT) images, etc. Another example of data input 102 may be orders from a medical facility or a doctor for these images. Another example of data input 102 may include lab results associated with the patient's blood work and may include lab tests, sodium data, potassium data, cholesterol data, etc. Yet another example of data input 102 may include data associated with the patient's diet or the number of times a patient has been admitted or readmitted to the hospital over the patient's lifetime or within a predefined time period, etc. In other words, data input 102 may be data that is being generated around current or previous care of a patient from various computing systems, computer devices, and/or medical devices as the patient is being treated.

Data input 102 may include structured data or unstructured data. Structured data may be data that is organized in tables, rows, columns, or another structured format. Structured data may be quantitative data generated by medical devices, included in test results, vital signs, structured numeric output from various monitors, etc. Unstructured data may be written or spoken data, such as audio data, words written on doctor's notes, text data and/or image data.

Data input 102 may be stored in a memory storage 104, such as a database or another storage conducive to storing large amounts of data. Memory storage 104 may include patient profiles of thousands, if not millions, of patients that are or have previously been treated at a medical facility. Data input 102 for a particular patient may be associated with a patient profile as data input 102 is being stored in memory storage 104. In addition to data input 102, memory storage 104 may store historical data of a patient. Historical data may be any data that has been previously received and stored in memory storage 104 that is associated with the previous medical history of the patient, such as data from previous admissions to a medical facility or previous treatments, or from a current admission to the medical facility but from a time that has been received and stored in memory storage 104 earlier than the current time, or from prior ambulatory encounters or prior patient generated data (e.g., wearable data, patient's personal medical record, home-based sensor data, and the like).

In some embodiments, prior to storing data input 102 in memory storage 104, data input 102 may be validated, translated, and normalized into a format that may be stored in memory storage 104 and processed by other components in patient management system 100A.

In some embodiments, memory storage 104 may be accessible over a network 106. Network 106 may be implemented as a single network or a combination of multiple networks. For example, in various embodiments, network 106 may include the Internet or one or more intranets, landline networks, wireless networks, and/or other appropriate types of networks. Network 106 may be a small-scale communication network, such as a private or local area network, or a larger-scale network, such as a wide-area network.

In some embodiments, patient management system 100A may include an application server 108. Application server 108 may be an enterprise server or cloud server or the like. Application server 108 may receive and process various patient data, including structured and unstructured patient data, such as patient data stored in memory storage 104. Applicant server 108 includes an artificial intelligence (AI) engine 112 that may correlate the patient data gathered from multiple devices with a knowledge base of medical treatment options, diagnostics, and other related information to generate a patient summary. Once AI engine 112 processes patient data, application server 108 may generate data output 113. Example data output 113 may be patient summaries 114 that include data that is ranked, prioritized, limited for purposes of generating summarizations, and sent to computing devices 122 of various different interested entities, including, but not limited to, primary care physicians, surgeons, specialist physicians, pharmacists, close family members, extended family members, nurses, out-patient facilities, and other members of the medical facility. Patient summaries 114 may be associated with a patient profile and may be stored in memory storage 104. Notably, application server 108 is included for illustrative purposes only, and another computing device may be utilized instead of application server 108.

AI engine 112 executing within application server 108 receives data input 102 and generates data output 113 such as patient summary 114. Summary 114 may include patient conditions 116, diagnostics and diagnoses 118 performed or recommended to determine additional conditions, and treatments 120 for known conditions including both chronic and short-term conditions.

Summary 114 may be displayed on computing devices 122. Computing devices 122 may be user devices under control of end users. Computing devices 122 may receive updates and/or provide access to the patient information, including summaries 114. Example computing devices 122 may be laptop computers, desktop computers, smartphones, tablets, etc. Computing devices 122 may be communicatively connected to network 106 and receive and display summaries 114 that are stored in memory storage 104 or request and receive summaries 114 from application server 108. Computing devices 122 may receive input from various parties, including a patient, family of the patient, doctors, nurses, medical students, residents, out-patient care facility, pharmacy, home-based sensors, etc. In some instances, computing device 122 may send a request message to AI engine 112 to generate summary 114. The request message may include an identifier that identifies computing device 122 as being associated with a type of a user, e.g., patient or patient's family, or a medical professional such as a doctor, a nurse, pharmacist, or a medical student. Based on the user identifier, AI engine 112 may generate summary 114 that is directed to the type of user.

Figure 1B:
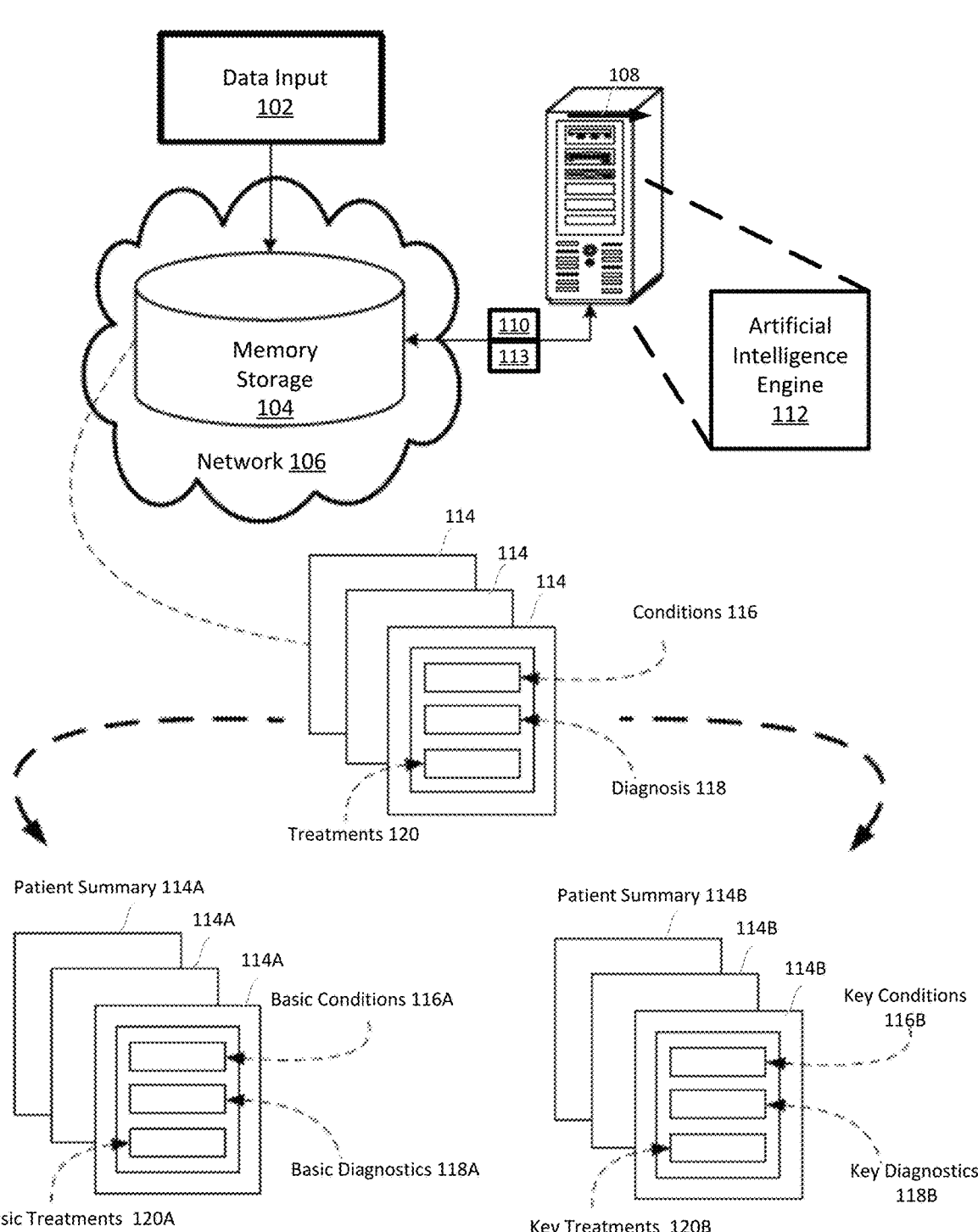

FIG. 1B is a block diagram of a patient management system 100B that generates summaries directed to a patient and to a medical professional, according to some embodiments. For example, AI engine 112 may generate summary 114A that includes patient summary in layman's terms and that is directed to one or more patients or their family members. Summary 114A may include basic patient information in layman language, such as basic conditions 116A (e.g., sick, pneumonia, etc.), basic diagnostics 118A (e.g., sputum sample) and basic treatments 120A (e.g., fluids, antibiotics). The medical summary 114B directed to medical professionals, such as during a handover from a physician-to-physician, doctor-to-nurse, etc., may include patient information in medical terms, such as key conditions 116B (e.g., tachycardia, pneumonia, sepsis), various key diagnostics 118B (e.g., sputum sample), and key treatments 120B (e.g., antibiotics—Azithromycin, Amoxicillin).

Figure 1C:
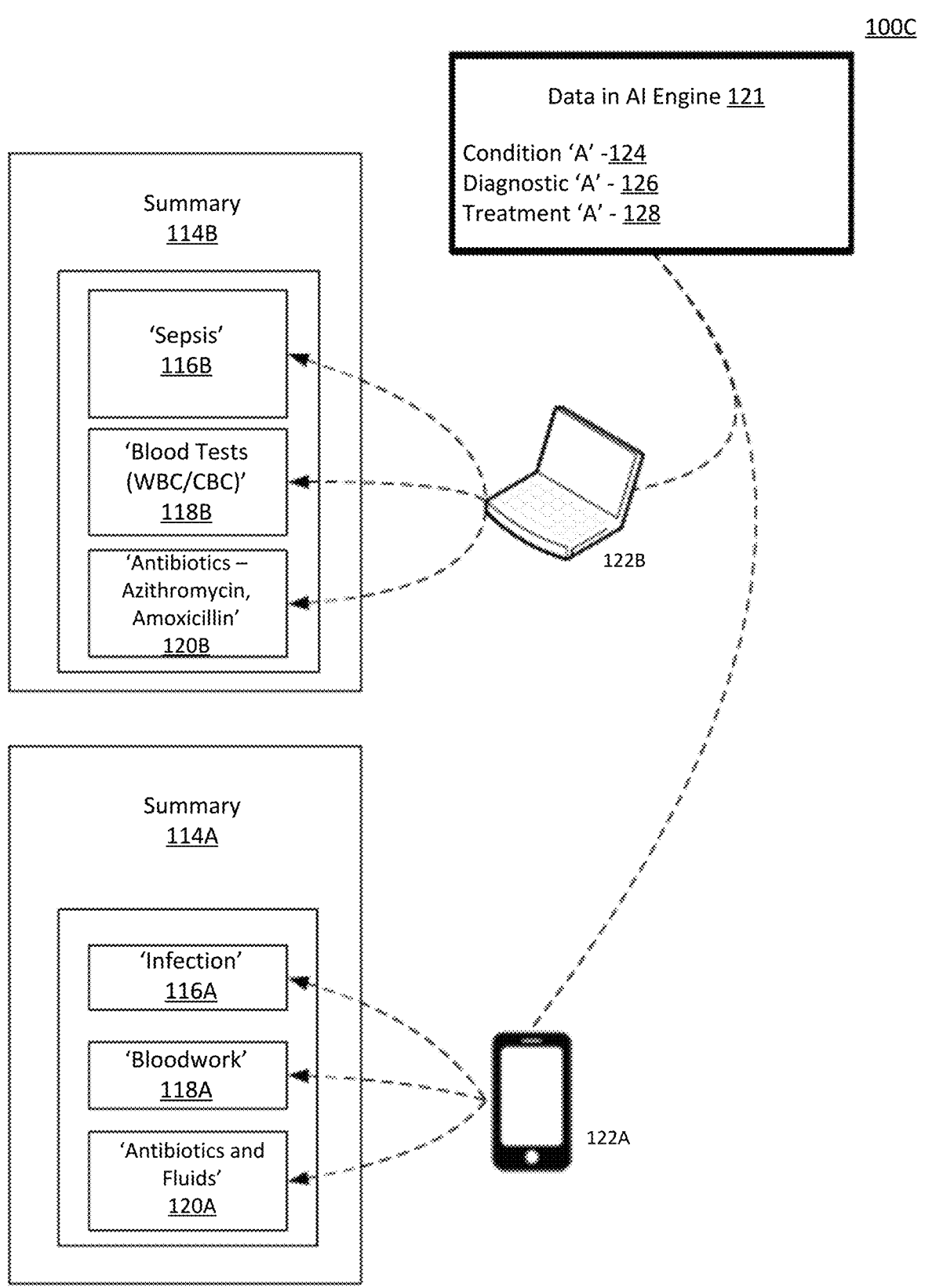

FIG. 1C illustrates a block diagram of a patient management system 100C further illustrating summaries that are directed to a patient and to a medical professional, according to some embodiments. FIG. 1C illustrates raw data 121 that may be stored in AI engine 112 during processing. Raw data 121 includes conditions 'A' 124, diagnostic 'A' 126 and treatments 'A' 128 that AI engine 112 identified but that have not yet summarized into summaries 114. Once AI engine 112 generates summaries 114 from raw data 121, summaries may be displayed on computing devices 122, such as a patient device 122A and physician device 122B.

The patient's or family member's device 122A may receive and display to a patient or patient's family summary 114A. The information in summary 114A may describe conditions 116A, diagnostics 118A and treatments 120A in a natural language directed to a patient, such as a general infection for condition 116A (e.g., HIV, COVID-19), diagnostics 118A (e.g., bloodwork), and treatments 120A (e.g., antibiotics and fluids).

The physician device 122B may receive and display to a medical professional summary 114B, which may occur during a medical team-to-medical team handover, physician-to-physician handover, a physician-to-nurse handover, or as requested for review by a medical professional. The medical professional summary may also be directed to medical student as a guide that teaches underlying patient conditions and proposed tests and/or treatments. The list of key conditions 116B, diagnostics 118B and treatments 120B shown in summary 114B may include 'Septembersis', 'Blood tests' for WBC/CBC and 'Antibiotics-Azithromycin, Amoxicillin', respectively. The language in key conditions 116B, diagnostics 118B and treatments 120B shown in summary 114B is synonymous with the language in conditions 116A, diagnostics 118A and treatments 120A, but includes medical terms because summary 114B is directed to a medical professional. Notably, the wording, the language, and the listings in summaries 114A-B are for exemplary purposes only, may be customized for the audience, and are accurate but different to accommodate various parties. Summaries 114A-B may be automatically generated and forwarded to the parties registered with the patient management system 100C.

In some embodiments, the key conditions 116B, diagnostics 118B and treatments 120B illustrated in summary 114B may be a subset of all contents of the patient's health record (which may number in thousands of pages of data) into a one to three sentence summary that highlights the active conditions, key pending and/or completed diagnostics, and key treatments. To do so, AI engine 112 may prioritize data and omit items from summary 114 of less importance (e.g., previous conditions, nonvital conditions, etc.) and includes items of relatively more importance (e.g., active conditions, vital treatments, etc.).

Figure 2:
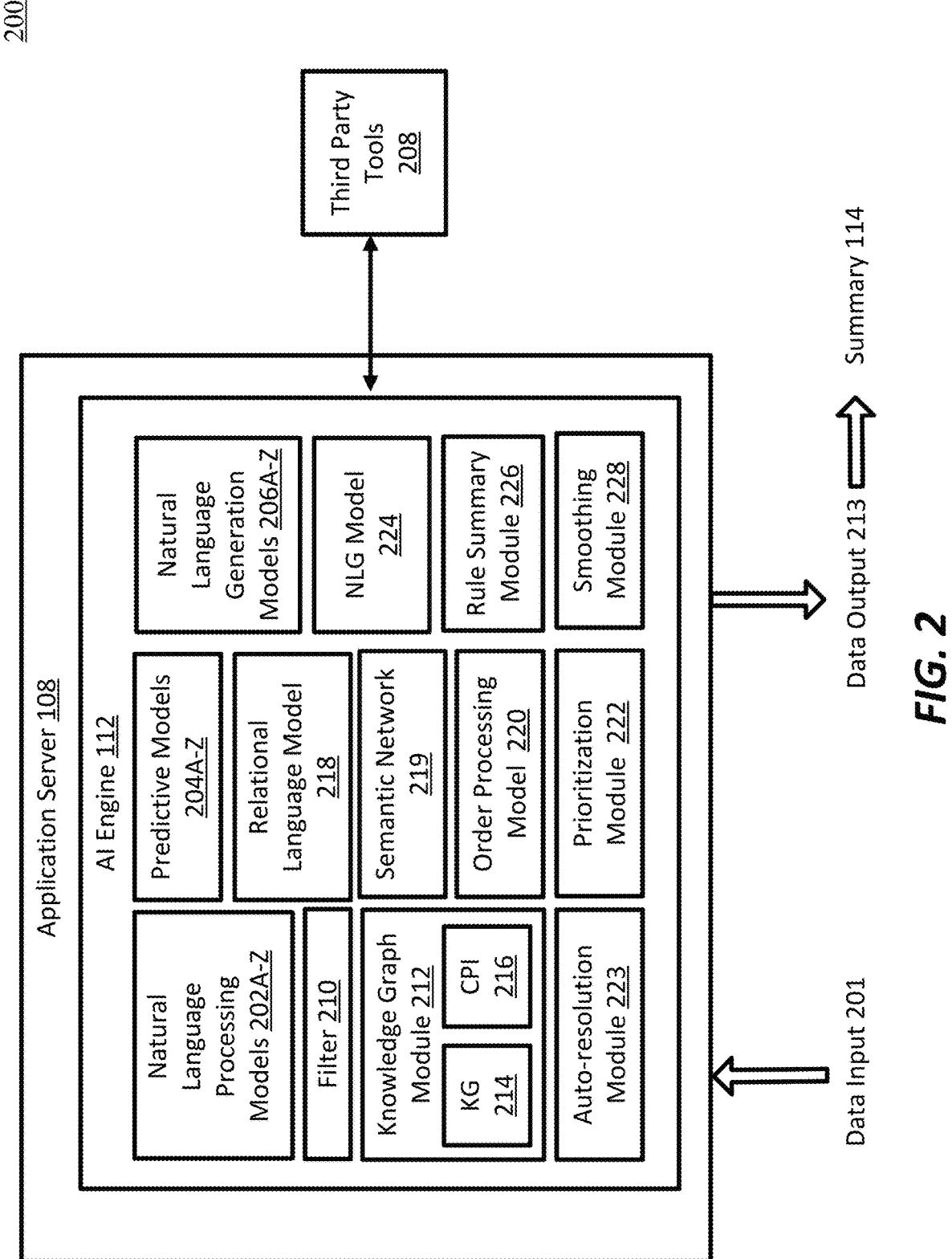
FIG. 2 is a block diagram of an artificial intelligence engine for generating patient summaries, according to some embodiments.

FIG. 2 is a block diagram 200 of an artificial intelligence (AI) engine, according to some embodiments. As discussed above, AI engine 112 may be included in application server 108 or be located on another computing device. AI engine 112 may receive data input 201 and generate data output 213. Data input 201 may be data associated with a patient such as current and historical patient data that is stored in memory storage 104 of FIG. 1. Data input 201 may also be a subset of patient data. As discussed above, data input 201 may include structured data and unstructured data. Data output 213 may be a summary of the patient conditions, diagnostics, and treatments, such as summary 114.

In some embodiments, AI engine 112 may include various components and modules that use natural language processing, machine learning, statistical analytics, etc., to generate data output 113 from data input 201. Each of the components and modules in AI engine 112 may be trained to perform a particular task or a combination of tasks. The training may occur using historical patient data or other types of datasets, including datasets that may be accessible over network 106 of FIG. 1. Once trained, the components and modules may receive and process data input 201 associated with a patient.

In some embodiments, AI engine 112 may include one or more of natural language processing (NLP) models 202, such as models 202A-Z. NLP models 202 may be recurrent neural network (RNN) models, neural net models including convolutional neural network (CNN) models, Bidirectional Encoder Representations from Transformers (BERT) models or their variants, and/or Generative Pre-trained Transformer (GPT) models, GPT-2 models, GPT-3 models and the like.

NLP models 202 may be pre-trained or trained on training data during a training phase. The training data may be data input 201 stored in storage memory 104 and may be historical data associated with numerous patients, their conditions, treatments and corresponding known outcomes. NLP models 202 may receive training data and may be trained on the training data until the NLP models 202 generate an expected outcome. Different NLP models 202 may be trained to process different tasks. These tasks are described in detail below.

Some NLP models 202, such as BERT models may be pre-trained to process natural language, e.g., human language, and perform pre-trained tasks, such as question answering, document summarization, sentence prediction, and dialogue or conversation responses. BERT models typically understand the context and sentiment of the language and are pre-trained to predict the next word in a sentence. The pre-trained BERT models may then be fine-tuned to process certain types of text, such as medical text, scientific text, etc. These types of BERT models may be bioBERT models that are pre-trained on biomedical training data, SciBERT models that are trained on scientific text, and docBERT models that are trained to process and classify certain documents. Some BERT models in NLP models 202, may also be fine-tuned on custom training data, such as medical data, patient's conditions, treatments, etc., that may be generated from historical patient data stored in memory storage 104.

Some NLP models 202 may be GPT, GPT-2 or GPT-3 models, collectively referred to as GPT models. The GPT models may be autoregressive language models. These models use deep learning networks that produce human-like text in a natural language. GPT models are trained on a training dataset that is generated by crawling the Internet as well as medical and scientific text.

NLP models 202 may be trained together or separately on various training datasets. The training datasets may be specific to a particular task associated with a corresponding NLP model 202A-Z. Once trained, NLP models 202 may enter an inference stage. During the inference stage, NLP models 202 may receive data input 201 which is data associated with a patient. Data input 201 may be current patient data, that is data associated with the patient since the last time AI engine 112 generated a summary for the patient. Data input 201 may also be integrated patient data that includes the entire history of the patient stored in memory storage 104. As there may be multiple NLP models 202 that are trained to process different tasks, each one of NLP models 202A-Z may process a subset of data input 201 that is associated with a task that the corresponding one of NLP models 202A-Z was trained to perform.

For example, an NLP model 202A may receive data input 201 that includes patient data, such as admission information, vital signs of the patient, respiratory rates, and/or doctor's notes or audio and identify the patient's reason for admission to the hospital or another medical care facility. In some instances, the NLP model 202A may also receive the patient's historical medical data, e.g., data from the previous hospital visits, as well as the patient's current data, and generate a reason for readmission to the hospital.

AI engine 112 may include context models, such as an NLP model 202B. NLP model 202B may receive data input 201 and detect concepts and attributes of the concepts. Example concepts may be medical problems, diagnoses, symptoms, treatments, medications, and lab results. Further examples of concepts may be negated phrasing, temporality (e.g., whether a condition is past or current), hypothetical, potential, or actual prognosis, and/or possessives (e.g., text referencing a patient or another family member).

In another example, some NLP models 202, such as an NLP model 202C and an NLP model 202D may be concept models. NLP model 202C may receive data input 201 that is associated with a patient and identify whether there are potential barriers to discharge. Example barriers to discharge may be pending tests or procedures associated with the patient, pending consultations, pending diagnostics, use of medications that may not be administered or are difficult to administer after discharge, etc. Upon receiving data input 201, NLP model 202C may generate an output that may be a classifier that indicates whether there is or is not a barrier to discharge. In another example, upon receiving data input 201, NLP model 202C may generate a classifier and a reason for the barrier to discharge, such as example reasons discussed above.

The NLP model 202D may receive data input 102 that is associated with a patient and generate an output that indicates potential social determinants that may affect the patient's health. For example, NLP model 202D may generate an output that is a classifier which indicates the existence of social determinants of health. The output may also include the determinants themselves. For example, NLP model 202D may be trained to identify one or more social determinants, such as housing instability, food insecurity, transportation needs, child care needs, etc., and may generate an output that includes those determinants. Notably, NLP models 202C and 202D are only examples of concept models and AI engine 112 may include other types of concept models not discussed above.

In another example, an NLP model 202E may indicate that a patient qualifies for a particular study or generate a list of patients that may qualify for a particular study. NLP model 202E may be trained on historical training data that includes patient symptoms that would qualify the patients for a particular study. Once trained, NLP model 202E may receive data input 201 that includes data of a patient, and may generate a list of patients that qualify for a study or an output that includes classifiers indicating whether a patient qualifies or does not qualify for the particular study.

In some embodiments, AI engine 112 may be communicatively connected to third-party tools 208. The third-party NLP tools 208 may receive output of NLP models 202, such as concepts generated using NLP model 202B. Example concepts may be problems, diagnoses, symptoms, treatments, medications, and lab results. One example of third-party tools 208 may be a Clinical Language Annotation, Modeling, and Processing Toolkit or CLAMP. CLAMP may receive concepts generated using one or more NLP models 202 and may map the concepts to UMLS (Unified Medical Language System), CUI (Concept Unique Identifiers), SNOMED CT (Systematized Nomenclature of Medicine—Clinical Terms), RxNorm, and LOINC® (Logical Observation Identifiers Names and Codes) as output. CLAMP may return the output back to the AI engine 112. Another example of the third-party tools 208 is AWS Amazon Comprehend Medical, which may receive the diagnoses generated using the NLP models 202 and may map the diagnoses to ICD-10 codes (International Classification of Diseases-10 codes), and return the ICD-10 codes to AI engine 112.

In some embodiments, AI engine 112 may include models that identify active clinical issues of a patient. An NLP model 202F, for example, may receive data input 201 which may be doctors' notes that include the patient's current medical issues, patient's historical data that may include patient's previous medical issues, output of other NLP models 202 and/or output of third-party software 208. Based on these inputs, NLP model 202F may identify active clinical issues associated with the patient. Specifically, NLP model 202F may select active clinical issues which may be a subset of all existing clinical issues of the patient as indicated by data input 201.

In some embodiments, from the active clinical issues and based on the historical data, NLP model 202F may remove or filter one or more active clinical issues. These may be clinical issues that have been negated in the past, clinical issues that may be associated with family members, etc. NLP model 202F may also understand the meaning of the concepts and remove duplicate concepts and/or similar concepts. For example, concepts Febrile and Fevers mean the same thing, and NLP model 202F may be trained to identify the same and/or similar concepts through the attributes associated with the third-party tools 208. For example, Amazon Comprehend Medical may map the identical or very similar diagnoses and symptoms to the same ICD-10 codes, and NLP model 202F may be trained to discard one of the concepts that is mapped to the same ICD-10 code. With respect to the Febrile and Fevers example, both Febrile and Fevers may be mapped to a ICD-10 code R50.9, one of which NLP model 202F may discard. In another example, NLP model 202F may use a similarity technique where the UMLS CUIs output from CLAMP may be used to compute similarity between two or more CUIs via CUI2VEC or another data similarity technique.

Alternatively, instead of NLP model 202F, AI engine 112 may include a filter 210. Filter 210 may receive input that includes current concepts identified using other NLP models 202 and historical patient data. Filter 210 may use rules to identify active concepts and remove duplicate or similar concepts using a set of predefined rules. For example, filter 210 may remove concepts that map to the same ICD-10 code, or may include a data similarity algorithm to remove the same or similar concepts.

Notably, new NLP models 202A-Z that are specific for processing different types of tasks, concepts, context, etc., may be continuously added to AI engine 112 to process data input 201 and generate output for the summary 114.

In some embodiments, AI engine 112 may include a knowledge graph (KG) module 212. KG module 212 may include a KG 214. KG 214 may be a knowledge graph that links clinical issues and their relationships, including links to other clinical issues, and/or treatments. For example, KG 214 may categorize relationships among medical problems, symptoms, procedures, and/or treatments. KG 214 may also rank which medical procedures and/or treatments are more important than others given a particular medical condition and/or symptoms. Some examples of KG 214 that may be included in KG module 212 may be UMLS, SNOMED CT, ICD-10 CPT, and the like. KG module 212 may receive an output of one or more NLP models 202, such as NLP model 202F or filter 210 that includes active clinical issues and traverse KG 214 to identify potential treatments. In some embodiments, KG module 212 may be communicatively connected to a clinical problem index (CPI) 216. The CPI 216 is an index stored in memory, such as memory of application server 108 or memory storage 104 of FIG. 1 or within KG module 212. CPI 216 may include an index that ranks clinical issues based on their severity. KG module 212 may use CPI 216 to determine which are key clinical issues and which are not key clinical issues given all the clinical issues identified based on the clinical issue rank.

In some embodiments, CPI 216 may use a statistical approach to score issues based on patients' outcomes, such as imminent deterioration, which may lead to critical outcomes, such as ICU admission or death. The clinical issues with a high score (e.g., over 90 out of a 100) may indicate they are more likely to induce critical outcomes, than the clinical issues with lower scores (e.g., less than 50 out of a 100).

In some embodiments, KG 214 may be generated using a relational language model 218. Relational language model 218 may identify relationships between clinical issues and treatments and generate KG 214 using the relationships. Relational language model 218 may also continue to modify KG 214 in real time as data from multiple patients becomes available. Relation language model 218 may receive input, such as a problem concept, and may output potentially related concepts with a desired semantic type (e.g., diuretics as a potential treatment) which are incorporated into KG 214. Relational language model 218 may be trained by a deep learning language modeling approach based on a large set of clinical notes. During training, the output of the relational language model 218 may be supervised by a clinician, physician, or data scientist.

In an alternative approach, KG 214 may be generated using a semantic network 219. Semantic network 219 may be a statistical and deep learning model that receives a concept as input and generates an output that is a related concept or treatment. Semantic network 219 may be trained and fine-tuned using training data with annotations.

AI engine 112 may include predictive models 204. Predictive models 204 may be one or more predictive models 204A-Z. Predictive models 204A-Z may receive data input 201 that includes structured data. Structured data may be patient data that includes vital signs, lab results, pending lab results, orders for tests or treatments, performed procedures, etc. Structured data may also include data generated using NLP models 202, third-party tools 208 and/or KG 214. Predictive XSmodels 204 may receive the structured data and generate risk scores that predict a patient's outcomes. In some instances, the score may be a probability score. Predictive models 204A-Z may be BERT models, long-short term memory (LSTM) models, neural network models, etc., that are pre-trained or trained to perform predictive tasks. Each predictive model 204A-Z may be trained to predict a different type of an outcome. Some non-limiting examples of the predictive models are discussed below.

For example, a predictive model 204A may generate a score that predicts when a patient will be discharged from a hospital. During a training phase, predictive model 204A may be trained on the historical outputs of the one or more NLP models 202A-Z until the output of the predictive model 204A matches (within a predefined range) the patient's historical data indicating whether the patient has or has not been discharged from the hospital. An example training dataset for predictive model 204A may include vital signs, lab results, pending lab results, orders for treatments, performed procedures and the like. The training dataset may be a dataset in a structured format.

In another example, a predictive model 204B may generate a score that predicts whether a patient will be readmitted to a hospital in the future. During a training phase, predictive model 204A may be trained on the historical outputs of the one or more NLP models 202A-Z until the output of the predictive model 204B matches (within a predefined range) the patient's historical data indicating whether the patient was or was not readmitted to the hospital. An example training dataset for predictive model 204B may include information associated with prior hospital utilization, including whether the patient has previously been readmitted to the hospital, the number of times the patient has been readmitted to the hospitals, the time intervals between hospital readmissions, etc. Additionally, the training dataset may include vital signs, lab results, pending lab results, orders for treatments, performed procedures and the like. The training dataset may be a dataset in a structured format.

In another example, predictive model 204C may receive the input of one or more NLP models 202A-Z and determine whether the patient's condition will deteriorate in the future or within a predefined time period. In some instances, predictive model 204C may be able to predict whether the patient's deterioration will be critical, e.g., whether there is a risk of sepsis. During a training phase, the predictive model 204C may be trained on the historical outputs of one or more NLP models 202A-Z until the output of the predictive model 204C matches (within a predefined range) the patient's historical data on whether the patient's condition will or will not deteriorate. An example training dataset for predictive model 204C may include vital signs, lab results, diagnoses, medical comorbidities, and the like. The training dataset may be a dataset in a structured format.

In another example, a predictive model 204D may receive the input of one or more NLP models 202A-Z and determine whether the patient will excessively utilize the health care system. Excessive utilization of the health care system may be a hospital stay over a predefined number of days, a number of hospital readmissions over a predefined number of readmissions, or excessive utilization of emergency services, such as utilization of an emergency room over a predefined number of times. During a training phase, predictive model 204D may be trained on the historical outputs of the one or more NLP models 202A-Z until the output of the predictive model 204D matches (within a predefined range) the patient's historical data that indicates whether the patient will or will not excessively use the hospital resources. An example training dataset for predictive model 204D may include vital signs, lab results, diagnoses, orders for tests or treatments, performed procedures, and past health care system utilization, and the like. The training dataset may be a dataset in a structured format.

Notably, new predictive models 204A-Z that are specific for predicting different scenarios may be continuously added to AI engine 112 to process the structured data in data input 201.

In some embodiments, AI engine 112 may include an order processing model 220. Order processing model 220 may receive structured data, such as data including diagnostic and treatment orders. Diagnostic orders may be orders for performing diagnostic procedures and treatment orders may be orders for treatment. Order processing model 220 may process the diagnostic and treatment orders based on when the orders are received. Order processing model 220 may use the BERT model to map the diagnostic and treatment orders to KG 214 and/or CPI 216. Using KG 214 and/or CPI 216, order processing model 220 may prioritize diagnostic and treatment orders to identify key diagnostics from the diagnostic orders and key treatments from the treatment orders, as well as reasons for the orders. For example, suppose order processing model 220 receives an order for an MRI that is associated with the patient. Order processing model 220 may use a BERT model to identify that the order is for an MRI and then map the MRI to the KG 214 and/or CPI 216 to prioritize the importance of the MRI order among other orders and diagnostics associated with the patient.

In some embodiments, AI engine 112 may include a prioritization module 222. Prioritization module 222 may receive active clinical conditions identified using NLP models 202, treatments identified using KG module 212, risk scores identified by predictive models 204, and pending key diagnostic orders and key active treatment orders identified by order processing model 220. Prioritization module 222 may prioritize treatments, pending diagnostic orders, and active treatment orders into a ranked list. Prioritization module 222 may also link the pending diagnostic orders and active treatment orders in the ranked list with the identified clinical issues.

In some embodiments, AI engine 112 may include an auto-resolution module 223. Auto-resolution module 223 may be trained to perform an auto-resolution task. The auto-resolution task may identify treatments that are no longer required, diagnostic orders that are no longer pending, and active treatment orders that have been fulfilled. The treatments and orders that are no longer required or have been fulfilled may be removed from the active clinical conditions and treatments before or after the treatments and/or orders are processed by prioritization module 222. In this case, prioritization module 222 may exclude or remove the identified treatment orders and diagnostic orders from the ranked list. In another example, auto-resolution module 223 may communicate with KG module 212 to determine which clinical issues and treatments have been resolved.

As discussed above, AI engine 112 includes NLG models 206, such as NLG models 206A-Z. NLG models 206 may be BERT models, GPT models, GPT-2 models, GPT-3 models, and the like. NLG models 206 may receive output from NLP models 202, predictive models 204, KG 214, and prioritization module 222 to generate an output that is a summary. There may be multiple NLG models 206 that are trained on different summary tasks, such that each model is trained to generate a summary for a particular summary task. For example, an NLG model 206A may be trained on a summary task to summarize key health issues or conditions of the patient. In another example, an NLG model 206B may be trained on a summary task to summarize treatments for the conditions. In another example, an NLG model 206C may be trained on a summary task to summarize the patients deterioration risk, and generate a deterioration score that corresponds to a low deterioration risk, high deterioration risk, or medium deterioration risk, as well as provide reasons for the risk. In another example, an NLG model 206D may be trained to summarize additional key diagnoses or key treatments that may be performed on the patient. In another example, an NLG model 206E may summarize patient information. In another example, NLG model 206F may be trained to recommend a clinical study for a patient.

In some embodiments, AI engine 112 may include NLG model 224. NLG model 224 may receive output from one or more of NLG models 206, which are summaries associated with a particular task, and generate an aggregate summary. NLG model 224 may be a BERT model, GPT model, GPT-2 model or GPT-3 model. In some embodiments, instead of receiving summaries from NLG models 206A-Z, NLG model 224 may receive output from NLP models 202, KG module 212, predictive models 204, and prioritization module 222 and generate a summary that summarizes patients' conditions, diagnoses, and treatment as a single summary.

In some embodiments, instead of NLG model 224, AI engine 112 may include a rule summary module 226. Rule summary module 226 may receive output from NLG models 206 and generate an output that is summary based on templates and rules. For example, rule summary module 226 may generate a summary using a set of rules that summarize concepts, diagnoses and treatments into a single summary.

In some embodiments, AI engine 112 may include a smoothing module 228. Smoothing module 228 may be a BERT model, GPT model, GPT-2 model or GPT-3 model. Smoothing module 228 may receive the output from NLG model 224 or rule summary module 226 and generate summary 114. For example, smoothing module 228 may rephrase or smooth the input and generate summary 114 that is directed to a particular audience. Example audiences may be a patient, a family member, or a medical professional, such as a doctor or a nurse. When smoothing module 228 generates summary 114 for a patient or a family member, smoothing module 228 may include a language in the summary 114 that summarizes in layman's terms the condition and/or treatment. Further, smoothing module 228 may adjust the language of the summary 114 depending on whether the summary 114 is directed to a patient or the patient's family member. When smoothing module 228 generates summary 114 for a medical professional, summary 114 may include medical terms associated with the patient's condition, diagnosis, and/or treatment. As discussed above, summary 114 that is directed to a medical professional may be generated during a handover, when the care of the patient is being handed over from one medical professional to another.

In some embodiments, smoothing module 228 may also generate summary 114 that is more empathetic when the summary 114 is directed to a patient or the patient's family member, rather than a medical professional.

In some embodiments, smoothing module 228 may also be trained as an adversarial model to detect or remove inappropriate language or words from the summary 114. Example inappropriate language may be words such as "suicide" or "kill," terms that may exhibit bias, and otherwise offensive language. Smoothing module 228 may also be trained on other tasks to remove other words or language from the summary 114.

Once smoothing module 228 generates summary 114, AI engine 112 may output summary 114 as data output 213.

Figure 3:
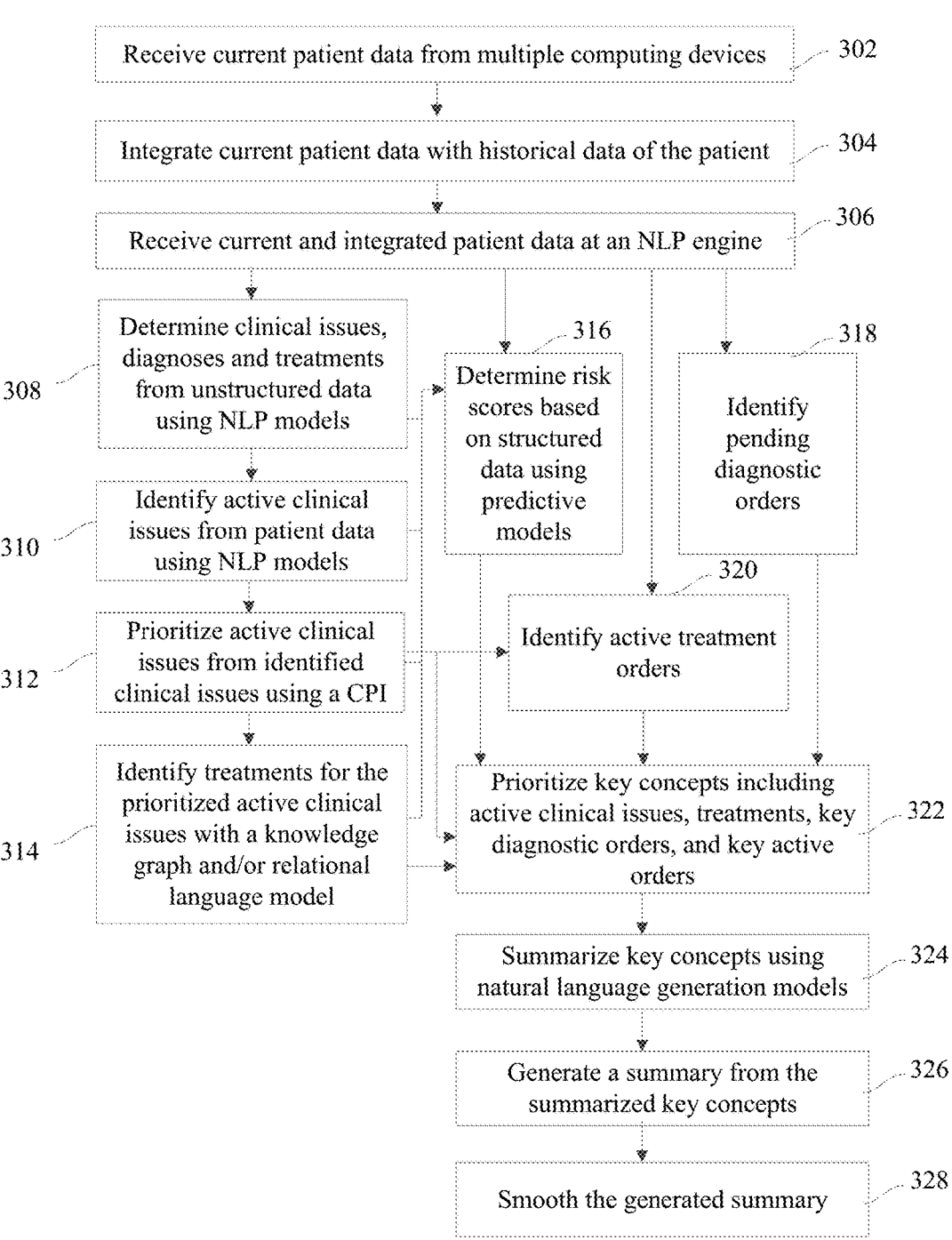
FIG. 3 is a diagram of a flow chart for generating patient summaries, according to some embodiments.

FIG. 3 is a diagram of a method 300 for generating a summary according to some embodiments. One or more of the processes 302-328 of method 300 may be implemented, at least in part, in the form of executable code stored on non-transitory, tangible, machine-readable media that, when run by one or more processors, may cause the one or more processors to perform one or more of the processes 302-328. Method 300 may occur as care around a patient is generated at a hospital or another facility and stored in memory storage 104. AI engine 112 may then query memory storage 104 at predefined intervals, upon request, or when memory storage 104 is updated with the patient data, and generate a summary of the patient conditions.

At operation 302, patient data is received. For example, memory storage 104 may receive data input 102. Data input 102 may be imported from an electronic health record (EHR) system and/or other data sources such as computing or medical devices that receive and/or collect patient data. Data input 102 may be current data associated with the care of the patient. Example current data may be data associated with a patient when the patient is admitted to a medical facility, data associated with the results of the diagnoses or tests, or data that includes notes or audio recording from a medical professional treating the patient. Current data may be new data that was generated since the last update of data input 102 to memory storage 104. Current data may also be data that was generated since a previous handover of a patient. In some instances, data input 102 may also be normalized into format consistent with how patient data is stored in memory storage 104.

At operation 304, patient data is integrated with the historical data of the patient. For example, data input 102 that represents current data associated with the patient may be integrated with historical data of the patient in memory storage 104. Historical data of the patient may include data from previous visits or admissions to the hospital, or data from the current admission to the hospital that has been entered into memory storage 104 earlier than the data input 102, such as data associated with previous diagnostics, previous doctor notes, previous treatments as a patient is being treated, or data that was stored in memory storage 104 prior to the time AI engine 112 generated summary 114. For example, suppose memory storage 104 stores historical data associated with a patient John Smith, who is 29 years old, with a past history of anxiety and asthma and a history of previous visits. John Smith is now being admitted to the hospital for tachycardia and HIV, which is data input 102.

John Smith may have a profile in memory storage 104 that includes historical and current data as follows:

a. Sepsis—Febrile to 102.9° F., dehydration, fevers, sinus tachycardia, medication induced tachycardia (medication albuterol).

b. Status post 3 L LR boluses in the ED with improvement from 150 s-120 s—atarax 25 mg q6 hr PRN for anxiety-continue to monitor on telemetry.

c. New diagnosis: HIV screen Ag/Ab screen positive on admission, associated with 15 pound weight loss.

d. Follow up CD4 count and HIV viral load Bilateral pulmonary opacities noted on imaging.

e. Differential includes edema vs. infectious etiologies. Concern for infectious etiologies, such as PJP and COVID Shortness of breath f. Low albumin at 2.7 with >1000 protein on UA.

During operation 304, data input received at operation 302 may be integrated with the historical data for John Smith that is stored in memory storage 104. Operations 302 and 304 may occur multiple times as the patient is being treated and data is generated around the care of the patient and entered into the EHR, lab results are received, physician notes are written, etc.

At operation 306, the data is received at an AI engine 112. For example, AI engine 112 may receive integrated patient data, current patient data, or a subset thereof, as data input 201. AI engine 112 may query memory storage 104 for data input 201 at predefined time intervals. Alternatively, memory storage 104 may provide data input 201 to AI engine 112 upon completion of operation 304. As discussed above, data input 201 may include unstructured and structured data. Unstructured data may be processed at operation 308. Structured data may be processed at operation 316. To an extent possible, AI engine 112 may process structured data and unstructured data in parallel.

At operation 308, unstructured data is processed. As discussed above, unstructured data may include data associated with doctors' handwritten or typed notes and/or audio recordings of a patient's conditions or symptoms. Unstructured data may also include image data, such as MRI data. Various NLP models 202 alone or in combination with third-party tools 208 may receive all or a portion of unstructured data and process the unstructured data according to the tasks associated with NLP models 202 and/or third-party tools 208. The NLP models 202 may be able to identify critical note types, note sections and note content associated with a patient, including the patient's conditions and current and past treatment. For example, from the unstructured data associated with the patient John Smith, NLP model 202A may be able to identify past medical history of anxiety, asthma and HIV positive status. NLP model 202B may identify admission to hospital due to persistent tachycardia and setting of HIV positive status. NLP model 202B may identify a concern about sepsis in light of high fever and tachycardia. NLP model 202B may identify a multifactorial nature of tachycardia given dehydration status, known anxiety iatrogenic (albuterol).

In another example, NLP model 202B may process the unstructured data to recognize treatments that are being undertaken to resolve the multiple clinical issues. For example, NLP model 202B may recognize that patient John Smith's tachycardia is being addressed with fluids (bolused with 2 L), that there is an improvement in tachycardia, and medication may be administered as needed to address anxiety.

In another example, NLP model 202B may process the unstructured data to recognize additional documented diagnostic investigations associated with a patient. For example, NLP model 202B may recognize that John Smith tested HIV Ag/Ab positive on admission, which likely accounted for noted weight loss. NLP model 202B may identify that there is a pending CD4 count and viral load assessment. NLP model 202B may identify indications that imaging shows significant interstitial opacities, that there is a concern for edema, infectious etiologies such as PJP, or COVID, low albumin protein count in blood, and high protein count in urine signifying kidney impact of system disease.

As discussed above, NLP models 202 alone, or in conjunction with third-party tools 208, may extract some or all concepts, including clinical issues, diagnoses, symptoms, treatments, etc., along with their attributes (e.g., section, negation, past, etc.) from the unstructured data. As also discussed above, NLP models 202C and 202D may extract concepts, such as potential barriers to discharge, social determinants of health, and disease identification. Further, NLP model 202B may detect attributes of the concepts, such as negated phrasing, temporality (e.g., past vs current), potentiality (e.g., potential or actual), and possessives (e.g., text in the unstructured data referencing the patient or a patient's family member).

At operation 310, active clinical issues may be identified. To identify active clinical issues, NLP model 202F may receive the output of NLP models 202 from operation 308 and current patient data and generate an output that includes active clinical issues. The current patient data may include note documents, audio data, etc., that was stored in memory storage 104 since the last patient update or the last time summary 114 was generated. NLP model 202F may identify the section of the note, audio, or other current patient data that is most relevant to the information task, and identify the active clinical issues for the patient based on the identified section of the data. Considering the example with John Smith that has a plethora of potential issues, NLP model 202F may identify the following active issues:

a. Tachycardia due to blood infection (sepsis), dehydration and anxiety.

b. Shortness of breath due to critical lung infection (PJP pneumonia causing sepsis) and secondarily to anxiety.

c. Infection in lung and infection in blood.

d. New HIV positive diagnosis with active infection with significant weight loss.

As part of operation 310, filter 210 may generate a subset of active clinical issues. For example, filter 210 may receive the active clinical issues and filter the active clinical issues that have been negated for the patient in the past or conditions that in the patient profile in memory storage 104 have been associated with a family member, but not the patient. As discussed above, filter 210 may include a set of rules that may be defined, updated, and/or deleted for filtering the active clinical issues. For example, suppose patient John Smith has a history of testing positive for tachycardia. Filter 210 may filter tachycardia because the issue has been previously negated by AI engine 112. Filter 210 may also include rules that deduplicate active clinical issues that are identical or very similar to each other. To distinguish the identical or similar concepts, filter 210 may include an ensemble of rules that are based on multiple options. One approach includes rules with the ICD-10 codes being mapped to identical or very similar diagnoses and symptoms. For example, as discussed above Febrile and Fevers have a similar meaning and both may be mapped to the ICD-10 code R50.9. In another example, filter 210 may include a machine learning network that determines data similarity between 2 or more CUIs, by determining embeddings of the CUIs and using a similarity algorithm to compute similarity score between the determined embeddings. Based on the similarity score (e.g., scores between zero and a low threshold above zero identify similar CUIs, whereas scores between a higher threshold and one identify dissimilar CUIs), filter 210 may identify similar CUIs and retain one of the active clinical issues associated with the similar CUIs.

At operation 312, active clinical issues are prioritized. For example, KG module 212 may receive active clinical issues and use CPI 216 to score the active clinical issues based on their severity. Based on the score, KG module 212 may determine which active clinical issues are key clinical issues and which issues are not key clinical issues. In a non-limiting example, KG module 212 may rank the scores associated with the active clinical issues in a descending order, and prioritize the active clinical issues with the scores above a predefined threshold or a top n number of clinical issues. For example, in the case of John Smith, KG module 212 may prioritize active clinical issues that include shortness of breath, Tachycardia, sepsis and pneumonia, and new and active HIV infection. In some instances, KG module 212 may prioritize active clinical issues based on a type of a user (e.g., physician, nurse, patient, family of patient) that may view summary 114 and the importance of those clinical issues to the respective user. KG module 212 may also prioritize active clinical issues based on the terms of the sign-out setting type (e.g., hospital, ambulatory, home). In some instances, auto-resolution module 223 may determine whether active clinical issues are resolved. If the active clinical issue is resolved, KG module 212 may exclude the active clinical issue from being prioritized.

At operation 314, treatments and diagnostic steps for the prioritized active issues are identified. For example, KG module 212 may traverse KG 214 for each prioritized clinical issue and identify proposed treatments and diagnostics. As discussed above, KG 214 includes clinical issues and problem-treatment relationships that may be used to identify the key clinical next steps as the therapies and/or diagnostics for the key clinical issues. For example, suppose KG 214 receives tachycardia as an active clinical issue for John Smith. KG 214 has a link between tachycardia and diuresing treatment. KG module 212 traversing KG 214 may recommend a diuresing treatment for the patient to treat tachycardia. KG module 212 may also indicate that a patient is waiting for a diagnostic, such as an echocardiogram for EF.

At operation 316, risk scores for a patient are determined from structured data. For example, as discussed above in operation 306, AI engine 112 may receive current and integrated patient data, which includes structured data. Structured data may be data that includes vital signs, lab results, pending lab results, orders for diagnostics or treatment, and performed procedures. In some instances, structured data may also have been generated in operations 308-314 and may be included in operation 316. With reference to John Smith, example structured data may be:

a. Flowsheets with vital signs, including temperature of 102 F (fever), pulse in the 100$s$ (tachycardia) among others.

b. Lab results: Positive HIV Ag/Ab, low WBC.

c. Pending Labs: CD4 count, viral load.

d. Orders: Broad spectrum antibiotics, chest imaging, sputum culture.

e. Procedures: bronchoalveolar lavage.

Predictive models 204 may generate risk scores from the structured data. For example, predictive model 240B may generate a score predicting the likelihood of readmission to a medical facility. Predictive model 204A may generate a risk score predicting the readiness for discharge. Predictive model 204C may generate a score indicative of clinical risk of deterioration, e.g., sepsis. Predictive model 204D may generate a score indicative of an excess health system utilization, length of stay, etc.

At operation 318, order assessment identifying key diagnostic orders is performed. For example, at operation 306, AI engine 112 may receive structured data that includes diagnostic orders to perform diagnostic procedures. At operation 318, order processing model 220 may identify key diagnostics from the diagnostic orders and prioritize the diagnostic orders according to relevance. Order processing model 220 may also identify a reason for the diagnostic orders. For example, the clinical status of John Smith is consistent with sepsis and pneumonia, due to an active HIV infection. To have a conclusive etiology of the clinical picture, other confirmatory diagnostic tests with reasons may be ordered by the clinical team and include a procedure to get a sputum sample (bronchoalveolar lavage) infectious work up, evaluation for PJP through sputum culture, COVID-19 PCR to confirm cause of sepsis and lung infection, and CD4 count and HIV viral load to confirm HIV as the underlying cause of the clinical status and to assess the severity of the infection.

At operation 320, order assessment identifying key treatment orders are performed. For example, at operation 306, AI engine 112 received structured data of a patient that included orders for medication. Order processing model 220 may identify key active treatment orders from the orders for medication and may prioritize the treatment orders according to relevance using KG module 212. For example, the clinical status of John Smith warranted active treatment orders to start to reverse the clinical deterioration course. These orders included intravenous hydration to improve tachycardia, broad spectrum antibiotics to fight infections, and repeat chest imaging studies to monitor treatment progress. Order processing model 220 may determine which treatment orders would treat key active clinical issues identified in operation 312 and rank the treatment orders according to the prioritized active clinical issues. The output of the order processing model 220 may include a ranked list of key active treatment orders.

In some embodiments, operations 316, 318, and 320 may be performed in parallel.

At operation 322, key concepts are prioritized. For example, prioritization module 222 may prioritize key concepts associated with a patient. Specifically, prioritization module 222 may receive active clinical conditions identified in operation 312, treatments identified in operation 314, risks identified in operation 316, pending diagnostic orders identified in operation 318, and active treatment orders identified in operation 320. Prioritization module 222 may prioritize treatments, pending diagnostic orders, active treatment orders and risks into a ranked list. Prioritization module 222 may also link the pending diagnostic orders and active treatment orders in the ranked list with the identified active clinical conditions.

At operation 324, the key concepts are summarized. As discussed above, AI engine 112 includes NLG models 206. NLG models 206 may receive the key concepts identified in operation 322, and summarize the key concepts. For example, NLG model 206F may summarize patient information, NLG model 206A may summarize active clinical issues, NLG model 206B may summarize treatments, NLG model 206D may summarize diagnostic orders and active treatment orders, and NLG model 206C may summarize risks. With respect to John Smith, NLG model 206F may generate a summary that John Smith is a "young male". NLG model 206A may generate a summary that John Smith is "HIV positive with active infection resulting in potentially critical symptoms (shortness of breath, dehydration, weight loss) and signs (fever, tachycardia) likely consistent with sepsis and or pneumonia (lung infection)". NLG model 206B may generate a summary that "active treatment (fluids, broad spectrum antibiotics) have been started to stabilize John". NLG model 206D may generate a summary that "workup to narrow down the etiology of his clinical picture and refine his treatment modalities is ongoing". NLG model 206F may conclude that "In general, John is starting to look better than on presentation".

At operation 326, a summary is constructed from the summaries generated in operation 324. The NLG model 224 may be dedicated to receive individual summaries generated in operation 324 and construct an aggregated summary. The aggregated summary may be a one- to three-sentence summary of the patient's current status, key issues and next steps. With reference to John Smith, NLG model 224 may aggregate summaries associated with John Smith in operation 324 and generate the following output:

"John Smith is a 29-year-old male who presented with tachycardia, pneumonia and sepsis in the context of a new, active HIV infection. Pneumonia is likely due to PJP or COVID-19. We are providing fluids to improve his tachycardia. Broad spectrum antibiotics were started while we work up the causative agent of his acute infection. Clinical status has improved since his admission yesterday."

Alternatively, rule summary module 226 may generate a similar aggregated summary using a rule—and template-based approach. As discussed above, rule summary module 226 may include rules for combining summaries associated with patient information, active clinical issues, treatments, and diagnostics. Each rule or template can be filled with the key concepts identified and used to generate a summary.

In operation 328, the summary may be smoothed. For example, smoothing module 228 may receive the summary output of operation 326 as input and generate summary 114A or 114B from the summary. Smoothing module 228 may include a temperature hyperparameter that may be set to vary the language output of smoothing module 228, such that smoothing module 228 may generate summary 114A directed to a patient or summary 114B directed to a medical professional. For example, the hyperparameter may be set to cause smoothing module 228 to generate summary 114A directed to the patient or the patient's family at a designated readability level:

"Your family member is here with sepsis (an infection in the blood) and possible pneumonia. He is being treated with fluids and antibiotics and tested for causes of his current condition. He appears to have improved from yesterday."

An example readability level may be a seventh grade readability level on a standard readability scale, such as Flesh-Kincaid readability formula, or another readability level.

In another example, the hyperparameter may be set to cause smoothing module 228 to generate summary 114B for John Smith:

"John Smith is a 29-year-old male, HIV positive with sepsis and pulmonary opacities, potentially from PJP or COVID. Treating with fluids; on broad spectrum antibiotics until results from infectious workup are available. Low oxygenation requirement. Improving from yesterday."

As discussed above, smoothing module 228 may include an empathy hyperparameter, which adjusts the summary 114 based on empathy. Smoothing module 228 may also generate a red-flag classifier that may indicate that inappropriate language (e.g., suicide, kill, narcotics, violence, die, etc.) may be included in summary 114. In this case, the generated summary 114 may be re-run through smoothing module 228 during another operation 328 (not shown) to remove the words that caused the red-flag classifier under certain user contexts or patient scenarios.

After method 300 completes, summary 114 may be displayed on a user device as illustrated in FIGS. 1A-1C.

Figure 4:
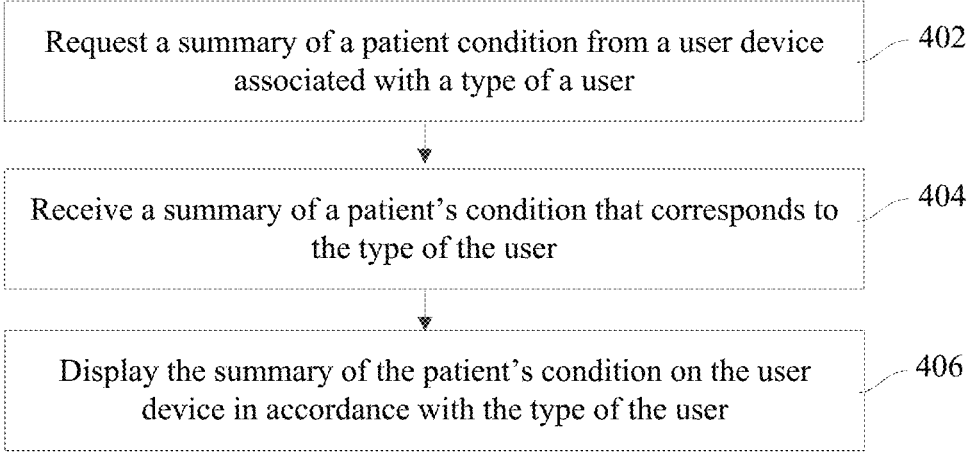
FIG. 4 is a diagram of a flow chart for displaying patient summaries, according to some embodiments.

FIG. 4 is a diagram of a method 400 for generating a summary for display on a user device, according to some embodiments. One or more of the processes 402-408 of method 400 may be implemented, at least in part, in the form of executable code stored on non-transitory, tangible, machine-readable media, that, when run by one or more processors, may cause the one or more processors to perform one or more of the processes 402-408. Method 400 may occur at predefined time intervals, as new patient data is generated around the care of a patient and stored in memory storage 104, upon request from computing device 122B of a medical professional, e.g., during a patient handover to another medical professional, or upon request from computing device 122A of a patient or patient's family.

At operation 402, a user device requests a summary. For example, computing device 122B associated with a medical professional or computing device 122A associated with a patient requests summary 114 from AI engine 112 by issuing a request message. The computing device 122A or 122B may issue a request for summary 114 in response to a patient handover or upon a request from the patient or the patient's family. In the request message, the computing device 122 may include an identifier that identifies that device or the user of the device as being associated with a user type, such as a user being a patient (or family member) or a medical professional.

At operation 404, a summary is received. For example, computing device 122 receives summary 114 from AI engine 112 in response to the request message. As discussed above, summary 114 summarizes patients' key conditions, key diagnoses and key treatments. Summary 114 may be summary 114A that may be displayed to a patient on computing device 122A and summarizes the patient's condition in layman's terms without medical terms or language. Summary 114 may be summary 114B that may be displayed on computing device 122B of a medical professional and summarizes the patient's condition in medical terms.

At operation 406, the summary is displayed. For example, summary 114A may be displayed on a user interface of computing device 122A or summary 114B may be displayed on a user interface of computing device 122B. Summary 114A or 114B may be displayed in a single paragraph that includes several sentences outlining the patient's condition, diagnoses and treatments. Alternatively, summary 114 may be divided into several paragraphs, one paragraph outlining the patient's condition, a second paragraph outlining the patient's diagnoses, and a third paragraph outlining the patient's treatment.

In some embodiments, AI engine 112 may be associated with configuration module 502. Configuration module 502 may be stored in a memory and be communicatively coupled to AI engine 112, be included within AI engine 112, or within one or more components within AI engine 112, such as KG module 212 or prioritization module 222 (not shown). Configuration module 502 may prioritize the information that is included in summary 114 discussed above using a summary level prioritization 504 and on a concept level prioritization 506. Further, both summary level prioritization 504 and concept level prioritization 506 may be configured differently depending on whether summary 114 is generated for a doctor, a patient, etc. Additionally, different configuration prioritizations may be added or removed from summary level prioritization 504 and concept level prioritization 506 than the prioritization configurations discussed below.

The summary level prioritization 504 may include a criticality and stability prediction configuration 508. KG module 212, prioritization module 222, and/or natural language generation models 206A-Z may use criticality and stability prediction configuration 508 to prioritize data in summary 114. Criticality and stability prediction configuration 508 may prioritize summary based on clinical deterioration prediction of a patient, followed by a discharge prediction. In some instances, summary 114 may display both clinical deterioration prediction and discharge prediction in the order specified by criticality and stability prediction configuration 508. In other instances, summary 114 may display clinical deterioration prediction only.

In another embodiment, summary level prioritization 504 may include a user based prioritization configuration 510. The user based prioritization configuration 510 may include configurations that prioritize the information in summary 114 based on the user type, such as a patient, family of the patient, doctor, nurse, medical student, resident, out-patient care facility, pharmacy, etc. Notably, there may be other summary level prioritizations that are not discussed above.

The concept level prioritization 506 may prioritize information in summary 114 on a more granular concept level. KG module 212, prioritization module 222, and/or natural language generation models 206A-Z may use concept level prioritization 506 to prioritize data in summary 114. Example configurations for concept level prioritization may be a barrier to discharge configuration 512, a key procedure configuration 514, and a key hospital event configuration 516. The barrier to discharge configuration 512 may prioritize information such as importance of the issue to discharge, auto resolution of the issue that is a barrier to discharge, e.g., whether the issue is pending or has been resolved, and/or similarity index that indicates how similar issues that are a barrier to discharge are. In some instances, after AI engine 112 applies the barrier to discharge configuration 512, summary 114 may display an issue that is the top barrier to discharge or the top n issues that are barriers to discharge, where n is an integer.

Key procedure configuration 514 may prioritize key procedures. In some instances, key procedure configuration 514 may prioritize the procedures according to the relevance of the key procedure to the key problem, whether the key procedures are being performed on the patient, have been ordered to be performed on the patient, or have been previously performed on the patient, and according to the key procedures identified using KG module 212. Notably, the prioritization in key procedure configuration 514 is exemplary and there may be other prioritizations that may be included in key procedure configuration 514.

Key hospital event configuration 516 may prioritize events based on events indicated by KG 214 and/or CPI 216, based on events that are current or have occurred in the past, etc. Notably, the key hospital event configuration 516 is exemplary and there may be other prioritizations that may be included in key hospital event configuration 516.

Figure 6B:
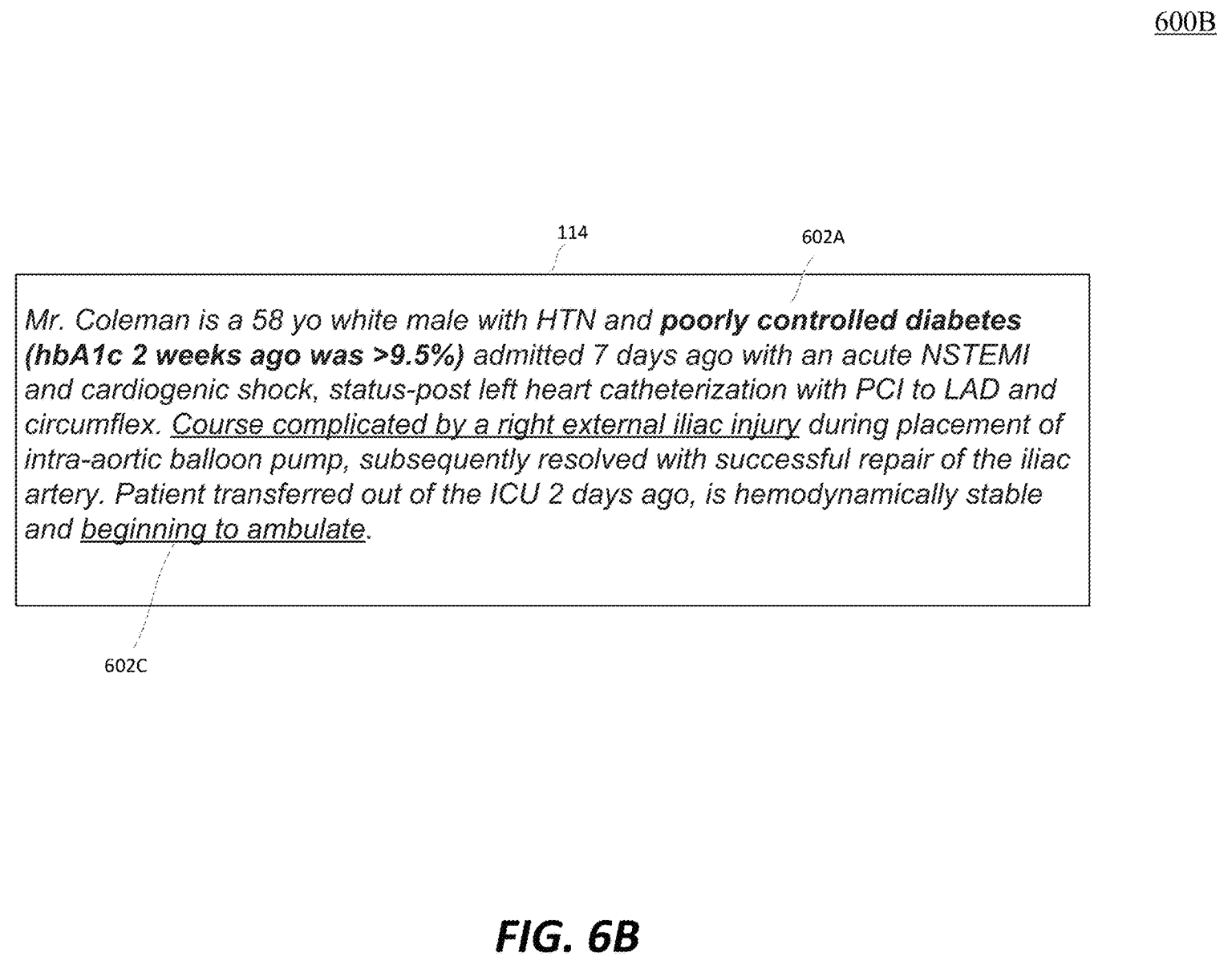

In some embodiments, summary 114 may include hyperlinks. FIGS. 6A and 6B are diagrams 600A and 600B of a summary that includes hyperlinks, according to some embodiments. A hyperlink in summary 114 may indicate that there is additional information that may be associated with a patient, but that is not displayed in summary 114. This information may be accessed via the hyperlink in the summary 114. FIG. 6A illustrates summary 114 that summarizes a condition of a patient named Mr. Coleman. Summary 114 includes hyperlinks 602A-C. Each one of hyperlinks 602A-C may receive instructions from a user via a user interface to be expanded or contracted. For example, suppose the user interface receives an instruction to expand hyperlink 602A, by e.g., clicking or tapping on the hyperlink 602A. FIG. 6B illustrates an expanded summary 114 that displays information included in hyperlink 602A in a parenthetical. Notably, the information associated with hyperlinks 602A-C may also be displayed in other ways, including as a standalone summary, in a separate text box, etc. Typically, hyperlinks 602A-C may be displayed in a different font, a different color or as underlying text to indicate that more information may be accessed and displayed using hyperlinks 602A-C. When a user interface receives instructions to contract summary 114, by e.g., clicking or tapping on hyperlink 602A, the summary 114 displayed in a user interface may revert to summary 114 displayed in FIG. 6A. In some embodiments, the information displayed using hyperlinks 602A-C may differ depending on whether a user is a medical professional, a patient, etc.

Figure 6C:
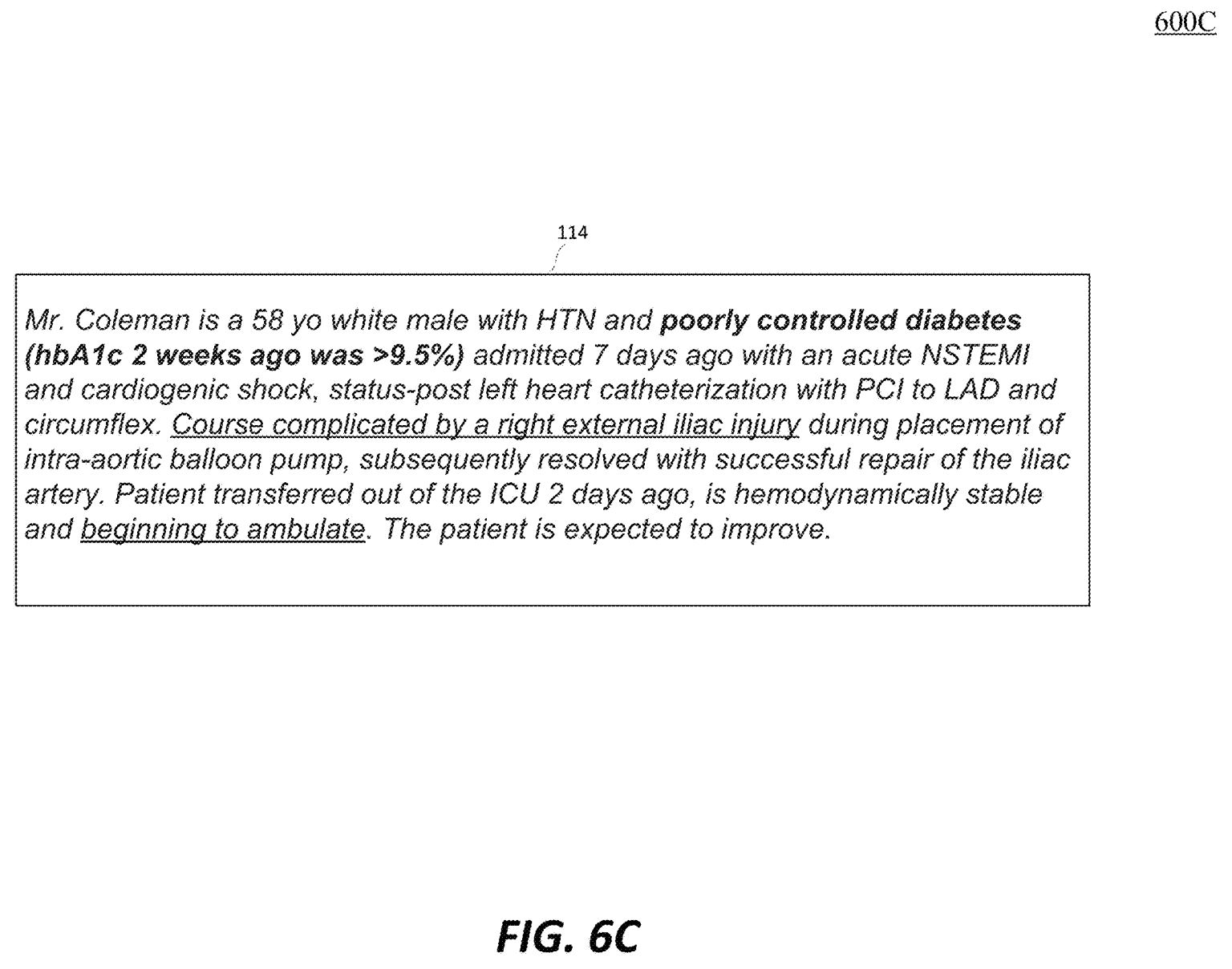

In some embodiments, summary 114 may be modified. For example, a medical professional may add, amend, or remove information from the summary 114. FIG. 6C is a block diagram 600C illustrating an updated summary, according to some embodiments. For example, computing device 122 may be used to add additional information to summary 114, such as "the patient is expected to improve." FIG. 6C displays summary 114 with the updated content. The computing device 122 may also be used to amend summary, such as changing the "right external iliac injury" to a "left external iliac injury," (not shown).

In some instances, summary 114 may be modified from some computing devices 122, but not others. For example, computing device 122, such as physician device 122B may be used to make changes to summary 114, while patient device 122A may be used to view, but not modify summary 114.

In some instances, summary 114 may be directed to an external out-patient facility or another entity. For example, suppose NLP model 202D discussed in FIG. 2 indicates that lack of food or lack of child care is a social determinant to the patient's health. In this case, AI engine 112 may generate summary 114 or a portion of the summary 114 that includes the social determinant to the patient's health. FIG. 6D is a diagram 600D that illustrates a summary that includes a social determinant to a patient's health, according to some embodiments. For example, when the patient, Mr. Coleman, discussed in FIGS. 6A-C, is about to be released from the hospital, summary 114 illustrated in FIG. 6D indicates that Mr. Coleman lives with a two year old child and requires child care services for the child. Summary 114 shown in FIG. 6D may be transmitted to a child care facility that may provide services to Mr. Coleman. In another example, summary 114 (not shown) may indicate that Mr. Coleman requires food deliveries twice a week over a one month period. This summary 114 may be transmitted to a third-party food facility that may provide food to Mr. Coleman. Because summary 114 discussed in FIG. 6D may be provided to third parties, summary 114 in FIG. 6D may be a standalone summary that is separate from the summary that includes the patient's medical conditions and is limited to one or more social determinants. In other embodiments, summary 114 in FIG. 6D may be appended to a summary that includes patient's conditions, such as summaries shown in FIGS. 6A-C.

The above embodiments may be implemented in hardware, in a computer program executed by a processor, in firmware, or in a combination of the above. A computer program may be embodied on a computer readable medium, such as a storage medium. For example, a computer program may reside in random access memory ("RAM"), flash memory, read-only memory ("ROM"), erasable programmable read-only memory ("EPROM"), electrically erasable programmable read-only memory ("EEPROM"), registers, hard disk, a removable disk, a compact disk read-only memory ("CD-ROM"), or any other form of storage medium known in the art.

Figure 5:
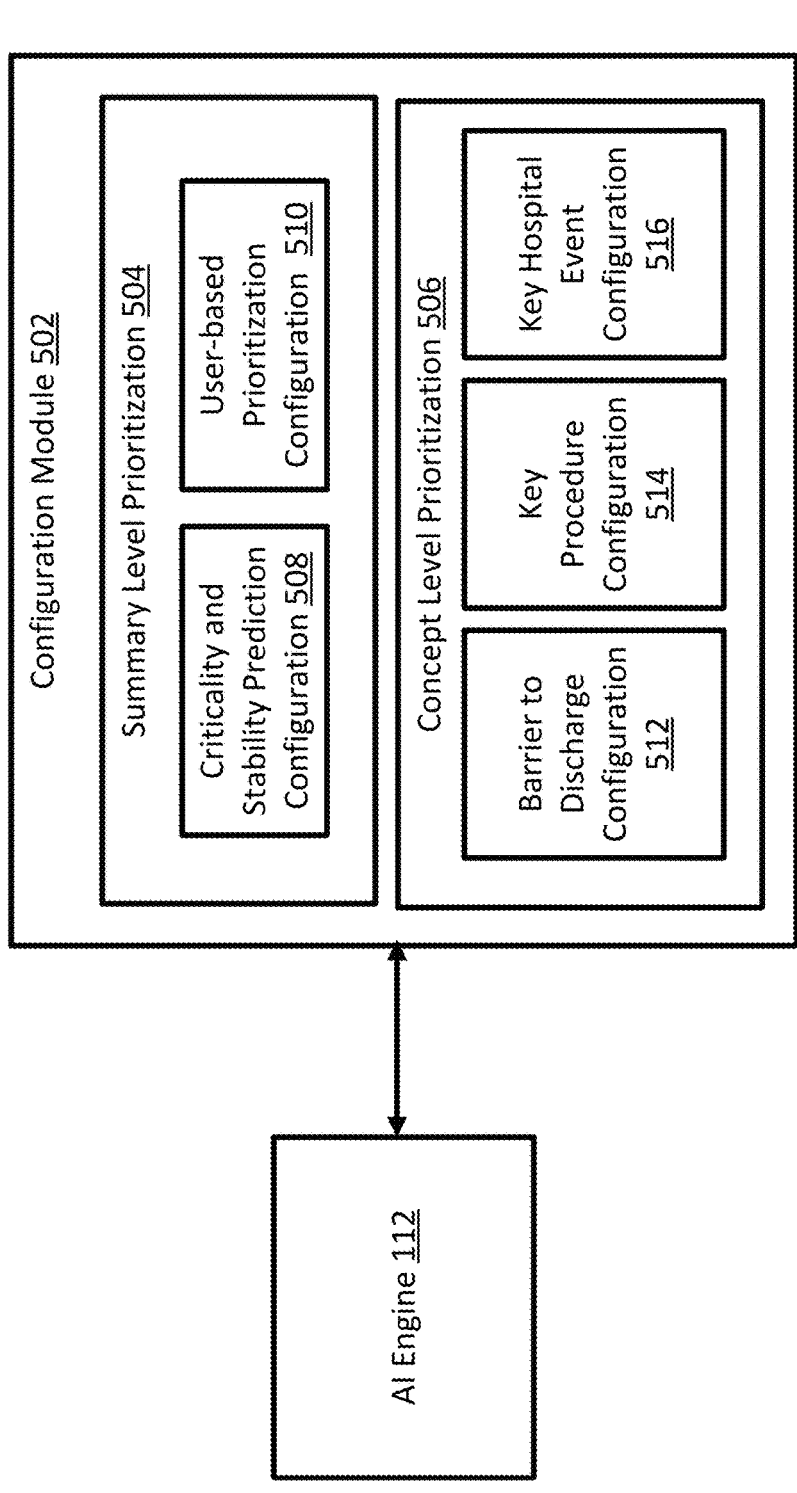
FIG. 5 is a diagram of a configuration module, according to some embodiments.

An exemplary storage medium may be coupled to the processor such that the processor may read information from, and write information to, the storage medium. In the alternative, the storage medium may be integral to the processor. The processor and the storage medium may reside in an application-specific integrated circuit ("ASIC"). In the alternative, the processor and the storage medium may reside as discrete components. For example, FIG. 5 illustrates an example computer system architecture 700, which may represent or be integrated in any of the above-described components, etc.

Figure 7:
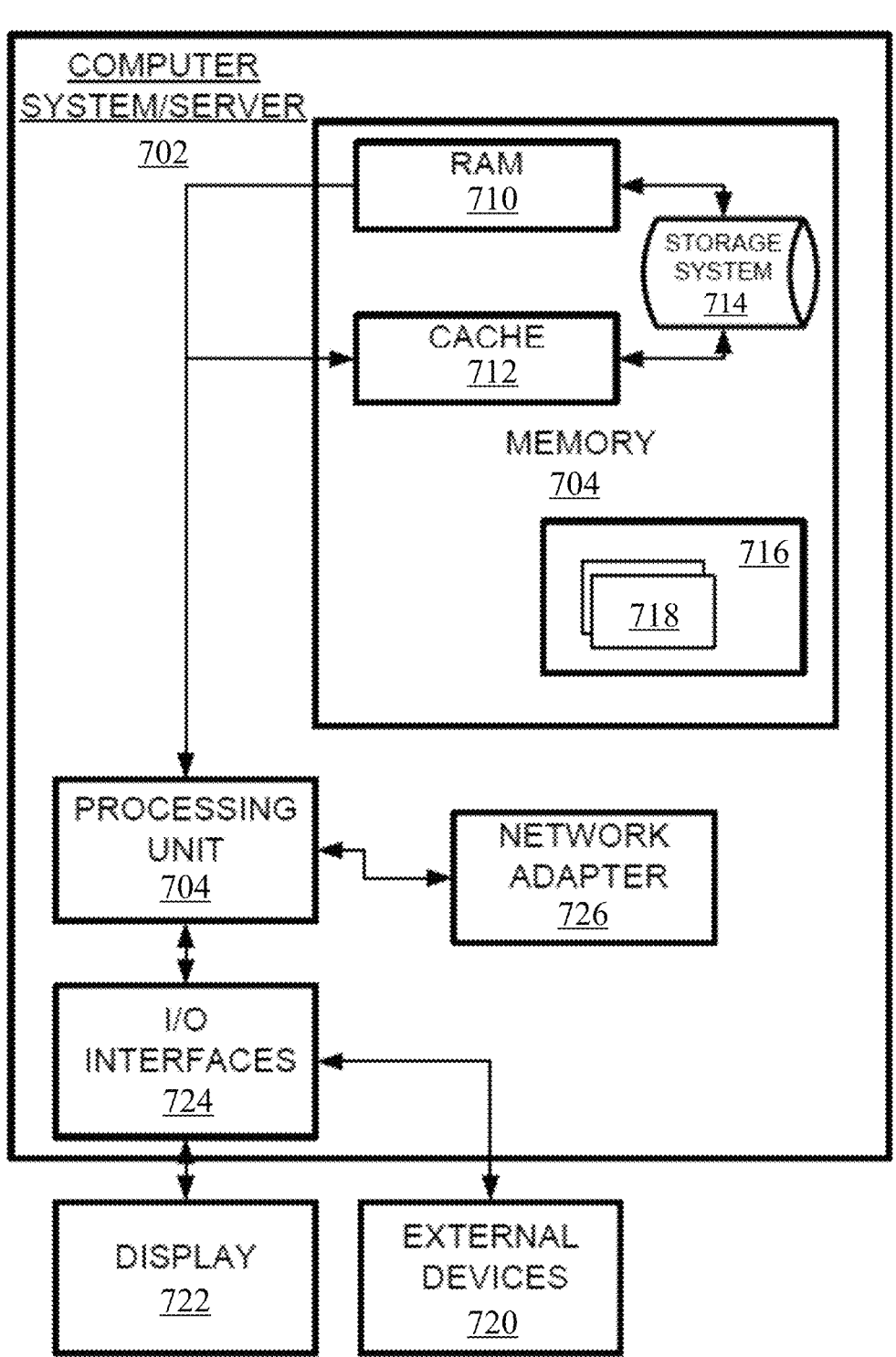
FIG. 7 illustrates an example network entity device configured to store instructions, software, and corresponding hardware for executing the same, where the embodiments may be implemented.

FIG. 7 is not intended to suggest any limitation as to the scope of use or functionality of embodiments of the application described herein. Regardless, the computing node is capable of being implemented and/or performing any of the functionality set forth hereinabove. In computing node 700, there is a computer system/server 702, which is operational with numerous other general purpose or special purpose computing system environments or configurations. Examples of well-known computing systems, environments, and/or configurations that may be suitable for use with computer system/server 702 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 702 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 702 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 7, computer system/server 702 in cloud computing node 700 is shown in the form of a general-purpose computing device. The components of computer system/server 702 may include, but are not limited to, one or more processors or processing units 704, a system memory 706, and a bus that couples various system components including system memory 706 to processor 704.

The bus represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 702 typically includes a variety of computer system readable media. Such media may be any available media that is accessible by computer system/server 702, and it includes both volatile and non-volatile media, removable and non-removable media. System memory 706, in one embodiment, implements the flow diagrams of the other figures. The system memory 706 can include computer system readable media in the form of volatile memory, such as random-access memory (RAM) 710 and/or cache memory 712. Computer system/server 702 may further include other removable/non-removable, volatile/non-volatile computer system storage media. By way of example only, memory 706 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to the bus by one or more data media interfaces. As will be further depicted and described below, memory 706 may include at least one program product having a set (e.g., at least one) of program modules that are configured to carry out the functions of various embodiments of the application.

Program/utility, having a set (at least one) of program modules, may be stored in memory 706 by way of example, and not limitation, as well as an operating system, one or more application programs, other program modules, and program data. Each of the operating system, one or more application programs, other program modules, and program data or some combination thereof, may include an implementation of a networking environment. Program modules generally carry out the functions and/or methodologies of various embodiments of the application as described herein.

As will be appreciated by one skilled in the art, aspects of the application may be embodied as a system, method, or computer program product. Accordingly, aspects of the application may take the form of an entirely hardware embodiment, an entirely software embodiment (including firmware, resident software, microcode, etc.) or an embodiment combining software and hardware aspects that may all generally be referred to herein as a "circuit," "module" or "system." Furthermore, aspects of the application may take the form of a computer program product embodied in one or more computer readable medium(s) having computer readable program code embodied thereon.

Computer system/server 702 may also communicate with one or more external devices 720 via a I/O interfaces 724, such as a keyboard, a pointing device, a display 722, etc.; one or more devices that enable a user to interact with computer system/server 702; and/or any devices (e.g., network card, modem, etc.) that enable computer system/server 702 to communicate with one or more other computing devices. Such communication can occur via I/O interfaces 724 of the adapter 726. Still yet, computer system/server 702 can communicate with one or more networks such as a local area network (LAN), a general wide area network (WAN), and/or a public network (e.g., the Internet) via network adapter. As depicted, adapter 726 communicates with the other components of computer system/server 702 via a bus. It should be understood that although not shown, other hardware and/or software components could be used in conjunction with computer system/server 702. Examples include, but are not limited to: microcode, device drivers, redundant processing units, external disk drive arrays, RAID systems, tape drives, and data archival storage systems, etc.

Although an exemplary embodiment of at least one of a system, method, and non-transitory computer readable medium has been illustrated in the accompanying drawings and described in the foregoing detailed description, it will be understood that the application is not limited to the embodiments disclosed, but rather is capable of numerous rearrangements, modifications, and substitutions as set forth and defined by the following claims. For example, the capabilities of the system of the various figures can be performed by one or more of the modules or components described herein, or in a distributed architecture, and may include a transmitter, receiver, or pair of both. For example, all or part of the functionality performed by the individual modules may be performed by one or more of these modules. Further, the functionality described herein may be performed at various times and in relation to various events, internal or external to the modules or components. Also, the information sent between various modules can be sent between the modules via at least one of: a data network, the Internet, a voice network, an Internet Protocol network, a wireless device, a wired device and/or via plurality of protocols. Also, the messages sent or received by any of the modules may be sent or received directly and/or via one or more of the other modules.

One skilled in the art will appreciate that a "system" could be embodied as a personal computer, a server, a console, a personal digital assistant (PDA), a cell phone, a tablet computing device, a smartphone or any other suitable computing device, or combination of devices. Presenting the above-described functions as being performed by a "system" is not intended to limit the scope of the application in any way but is intended to provide one example of many embodiments. Indeed, methods, systems and apparatuses disclosed herein may be implemented in localized and distributed forms consistent with computing technology.

It should be noted that some of the system features described in this specification have been presented as modules, in order to more particularly emphasize their implementation independence. For example, a module may be implemented as a hardware circuit comprising custom very large-scale integration (VLSI) circuits or gate arrays, off-the-shelf semiconductors such as logic chips, transistors, or other discrete components. A module may also be implemented in programmable hardware devices such as field programmable gate arrays, programmable array logic, programmable logic devices, graphics processing units, or the like.

A module may also be at least partially implemented in software for execution by various types of processors. An identified unit of executable code may, for instance, comprise one or more physical or logical blocks of computer instructions that may, for instance, be organized as an object, procedure, or function. Nevertheless, the executables of an identified module need not be physically located together but may comprise disparate instructions stored in different locations which, when joined logically together, comprise the module and achieve the stated purpose for the module. Further, modules may be stored on a computer-readable medium, which may be, for instance, a hard disk drive, flash device, random access memory (RAM), tape, or any other such medium used to store data.

Indeed, a module of executable code could be a single instruction, or many instructions, and may even be distributed over several different code segments, among different programs, and across several memory devices. Similarly, operational data may be identified and illustrated herein within modules and may be embodied in any suitable form and organized within any suitable type of data structure. The operational data may be collected as a single data set or may be distributed over different locations including over different storage devices, and may exist, at least partially, merely as electronic signals on a system or network.

It will be readily understood that the components of the application, as generally described and illustrated in the figures herein, may be arranged and designed in a wide variety of different configurations. Thus, the detailed description of the embodiments is not intended to limit the scope of the application as claimed but is merely representative of selected embodiments of the application.

One having ordinary skill in the art will readily understand that the above may be practiced with steps in a different order, and/or with hardware elements in configurations that are different than those which are disclosed. Therefore, although the application has been described based upon these preferred embodiments, it would be apparent to those of skill in the art that certain modifications, variations, and alternative constructions would be apparent.

While preferred embodiments of the present application have been described, it is to be understood that the embodiments described are illustrative only and the scope of the application is to be defined solely by the appended claims when considered with a full range of equivalents and modifications (e.g., protocols, hardware devices, software platforms etc.) thereto.

While example embodiments have been particularly shown and described, it will be understood by those skilled in the art that various changes in form and details may be made therein without departing from the scope of the embodiments encompassed by the appended claims.

What is claimed is:

1. A system comprising:

a memory configured to store instructions for an artificial intelligence engine;

a processor coupled to the memory and configured to read the instructions from the memory to cause the system to perform operations, the operations comprising:

receiving, over a network, patient data associated with a patient, the patient data including unstructured data collected from multiple computing systems, wherein the unstructured data includes at least audio data;

determining, using a plurality of natural language processing models in the artificial intelligence engine, a plurality of clinical issues of the patient based on the audio data;

summarizing, using a plurality of natural language generation models in the artificial intelligence engine that are each trained to generate a summary for a different summary task, the clinical issues into a plurality of notes that are different from each other;

aggregating, using an aggregating natural language generation model in the artificial intelligence engine, the plurality of notes into one or more aggregate notes associated with the patient, wherein the one or more aggregate notes are in a paragraph form;

smoothing, using the aggregating natural language generation model that includes a hyperparameter set to vary a language output of the aggregating natural language generation model based on a target audience, the one or more aggregate notes into smoothed one or more notes by rephrasing the one or more aggregate notes for the target audience; and transmitting the smoothed one or more notes for display on at least one computing device.

2. The system of claim 1, wherein the patient data includes structured data and further comprising:

generating, using at least one predictive neural network model and the structured data, at least one risk score, wherein the at least one risk score corresponds to a patient outcome;

generating, using one of the plurality of natural language generation models and the at least one risk score, a patient note corresponding to the patient outcome; and incorporating the patient note into the plurality of notes.

3. The system of claim 2, wherein the at least one risk score that corresponds to the patient outcome is a prediction of a patient discharge from a hospital.

4. The system of claim 2, wherein the at least one risk score that corresponds to the patient outcome is a prediction of a clinical risk of deterioration of the patient.

5. The system of claim 1, further comprising:

determining, using a knowledge graph, a plurality of treatments for the plurality of clinical issues; and prioritizing the plurality of treatments for the plurality of clinical issues.

6. The system of claim 5, further comprising:

determining, using an auto-resolution module, that a treatment in the plurality of treatments is not required;

removing the treatment from the plurality of treatments; and prioritizing the plurality of treatments without the removed treatment.

7. The system of claim 6, further comprising:

summarizing, using the plurality of natural language generation models, the prioritized plurality of treatments into a second plurality of notes; and aggregating, using the aggregating natural language generation model, the second plurality of notes into the one or more aggregate notes associated with the patient.

8. The system of claim 6, further comprising:

determining, using one of the plurality of natural language processing models, that one of the plurality of treatments is a barrier to discharge; and generating, using one of the plurality of natural language generations models, reasons for the barrier to discharge.

9. The system of claim 1, further comprising:

receiving an identifier in a message from the at least one computing device;

linking the identifier to a type of a user; and setting the hyperparameter based on the type of the user, wherein the smoothed one or more notes include different content depending on the hyperparameter.

10. A method comprising:

receiving, over a network, patient data associated with a patient, the patient data including unstructured data collected from multiple computing systems, wherein the unstructured data includes audio data from an audio file;

determining, using a plurality of natural language processing models in an artificial intelligence engine executing on a processor, a plurality of clinical issues of the patient based on the audio data;

summarizing, using a plurality of natural language generation models in the artificial intelligence engine that are each trained to generate a summary for a different summary task, the clinical issues into a plurality of notes that are different from each other;

aggregating, using an aggregating natural language generation model in the artificial intelligence engine, the plurality of notes into one or more aggregate notes associated with the patient;

smoothing, using the aggregating natural language generation model that includes a hyperparameter set to vary a language output of the aggregating natural language generation model based on a target audience, the one or more aggregate notes into smoothed one or more notes by rephrasing the one or more aggregate notes for the target audience; and transmitting the one or more aggregated notes for display on a computing device.

11. The method of claim 10, wherein the patient data includes structured data and further comprising:

generating, using at least one predictive neural network model and the structured data, at least one risk score, wherein the at least one risk score corresponds to a patient outcome;

generating, using one of the plurality of natural language generation models and the at least one risk score, a patient note corresponding to the patient outcome; and incorporating the patient note into the plurality of notes.

12. The method of claim 11, wherein the at least one risk score that corresponds to the patient outcome is a prediction of a patient discharge from a hospital.

13. The method of claim 11, wherein the at least one risk score that corresponds to the patient outcome is a prediction of a clinical risk of deterioration of the patient.

14. The method of claim 10, further comprising:

determining, using a knowledge graph, a plurality of treatments for the plurality of clinical issues; and prioritizing the plurality of treatments for the plurality of clinical issues.

15. The method of claim 14, further comprising:

determining, using an auto-resolution module, that a treatment in the plurality of treatments is not required;

removing the treatment from the plurality of treatments; and prioritizing the plurality of treatments without the removed treatment.

16. The method of claim 15, further comprising:

summarizing, using the plurality of natural language generation models, the prioritized plurality of treatments into a second plurality of notes; and aggregating, using the aggregating natural language generation model, the second plurality of notes into the one or more aggregate notes associated with the patient.

17. The method of claim 15, further comprising:

determining, using one of the plurality of natural language processing models, that one of the plurality of treatments is a barrier to discharge; and generating, using one of the plurality of natural language generations models, reasons for the barrier to discharge.

18. The method of claim 10, further comprising:

setting the hyperparameter based on an identifier corresponding to a type of a user associated with the computing device.

19. A non-transitory computer-readable medium storing instructions thereon, that when executed by a processor, cause the processor to perform operations, the operations comprising:

receiving, over a network, patient data associated with a patient, the patient data including unstructured data collected from multiple computing systems, wherein the unstructured data includes audio data;

determining, using a plurality of natural language processing models in an artificial intelligence engine, a plurality of clinical issues of the patient based on the audio data;

summarizing, using a plurality of natural language generation models in the artificial intelligence engine that are each trained to generate a summary for a different summary task, the clinical issues into a plurality of notes that are different from each other;

aggregating, using an aggregating natural language generation model in the artificial intelligence engine, the plurality of notes into one or more aggregate notes associated with the patient, wherein the one or more aggregate notes are in a paragraph form;

smoothing, using the aggregating natural language generation model that includes a hyperparameter set to vary a language output of the aggregating natural language generation model based on a target audience, the one or more aggregate notes into smoothed one or more notes by rephrasing the one or more aggregate notes for the target audience; and transmitting the smoothed one or more notes for display on at least one computing device.

20. The non-transitory computer-readable medium of claim 19, wherein the audio data is extracted from an audio file recorded at the at least one computing device, wherein the smoothed one or more notes include different content depending on the hyperparameter.

* * * * *